(12) United States Patent
Matsumoto et al.

(10) Patent No.: US 9,393,043 B2
(45) Date of Patent: Jul. 19, 2016

(54) SENSOR INSERTION DEVICE AND METHOD FOR OPERATING SAID DEVICE

(71) Applicant: TERUMO KABUSHIKI KAISHA, Tokyo (JP)

(72) Inventors: Atsushi Matsumoto, Kanagawa (JP); Takahiro Ohkoshi, Kanagawa (JP); Hideki Katsura, Tokyo (JP); Moriyuki Watanuki, Chiba (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/485,148

(22) Filed: Sep. 12, 2014

(65) Prior Publication Data

US 2015/0073238 A1 Mar. 12, 2015
US 2016/0008028 A9 Jan. 14, 2016

Related U.S. Application Data

(63) Continuation-in-part of application No. PCT/JP2013/054920, filed on Feb. 26, 2013.

(30) Foreign Application Priority Data

Mar. 13, 2012 (JP) ................................. 2012-056084

(51) Int. Cl.
*A61B 5/145* (2006.01)
*A61B 17/34* (2006.01)
(Continued)

(52) U.S. Cl.
CPC ............. *A61B 17/3468* (2013.01); *A61B 5/076* (2013.01); *A61B 5/1495* (2013.01); *A61B 5/14503* (2013.01); *A61B 5/14532* (2013.01); *A61B 5/72* (2013.01); *A61B 5/74* (2013.01); *A61B 5/742* (2013.01); *G01D 18/00* (2013.01); *A61B 5/002* (2013.01); *A61B 5/0071* (2013.01); *A61B 5/1486* (2013.01); *A61B 2560/0276* (2013.01); *A61B 2560/063* (2013.01)

(58) Field of Classification Search
CPC .......... A61B 5/145; A61B 5/74; A61B 5/746; A61B 2560/0266; A61B 5/0276
See application file for complete search history.

(56) References Cited

U.S. PATENT DOCUMENTS 5,390,671 A 2/1995 Lord et al.
5,954,643 A 9/1999 VanAntwerp et al.
(Continued)

FOREIGN PATENT DOCUMENTS

CN 101006936 8/2007
CN 102307518 1/2012
(Continued)

OTHER PUBLICATIONS

U.S. Appl. No. 14/493,684, filed Sep. 23, 2014, Matsumoto et al.
(Continued)

*Primary Examiner* — Eric Winakur
(74) *Attorney, Agent, or Firm* — Sheridan Ross P.C.

(57) ABSTRACT

A sensor inserting device includes a device main body and a push handle for moving a detector of a sensor and an insertion needle, with the sensor held coupled to the insertion needle, into the body of a patient. A transmitter, for processing a signal from the sensor, is set in the device main body. A cable, allowing transmission of a signal between the sensor and the transmitter, is connected to the sensor (12) and the transmitter.

20 Claims, 19 Drawing Sheets

(51) Int. Cl.
  *A61B 5/00* (2006.01)
  *A61B 5/07* (2006.01)
  *A61B 5/1495* (2006.01)
  *G01D 18/00* (2006.01)
  *A61B 5/1486* (2006.01)

(56) References Cited

U.S. PATENT DOCUMENTS

| | | | |
|---|---|---|---|
| 6,248,067 B1* | 6/2001 | Causey, III | A61B 5/14532 600/347 |
| 2002/0161288 A1 | 10/2002 | Shin et al. | |
| 2005/0143635 A1 | 6/2005 | Kamath et al. | |
| 2006/0247508 A1 | 11/2006 | Fennell | |
| 2007/0073129 A1 | 3/2007 | Shah et al. | |
| 2008/0234561 A1* | 9/2008 | Roesicke | A61B 5/1495 600/345 |
| 2009/0076360 A1 | 3/2009 | Brister et al. | |
| 2010/0280354 A1 | 11/2010 | Zhang et al. | |
| 2010/0324392 A1 | 12/2010 | Yee et al. | |
| 2011/0021889 A1 | 1/2011 | Hoss et al. | |

FOREIGN PATENT DOCUMENTS

| | | |
|---|---|---|
| EP | 2327984 | 6/2011 |
| JP | H07-275227 | 10/1995 |
| JP | 2002-503988 | 2/2002 |
| JP | 2005-524463 | 8/2005 |
| JP | 2008-506468 | 3/2008 |
| JP | 2009-508639 | 3/2009 |
| JP | 2010-538745 | 12/2010 |
| WO | WO 2010091005 | 8/2010 |

OTHER PUBLICATIONS

Official Action and Search Report (with English translation) for Chinese Patent Application No. 201380013884.8, dated Nov. 12, 2015, 21 pages.

Extended European Search Report for European Patent Application No. 13761979, dated Oct. 7, 2015. 5 pages.

Official Action for U.S. Appl. No. 14/493,684, mailed Dec 8, 2015, 6 pages.

Notice of Allowance for U.S. Appl. No. 14/493,684, mailed Mar. 18, 2016, 5 pages.

* cited by examiner

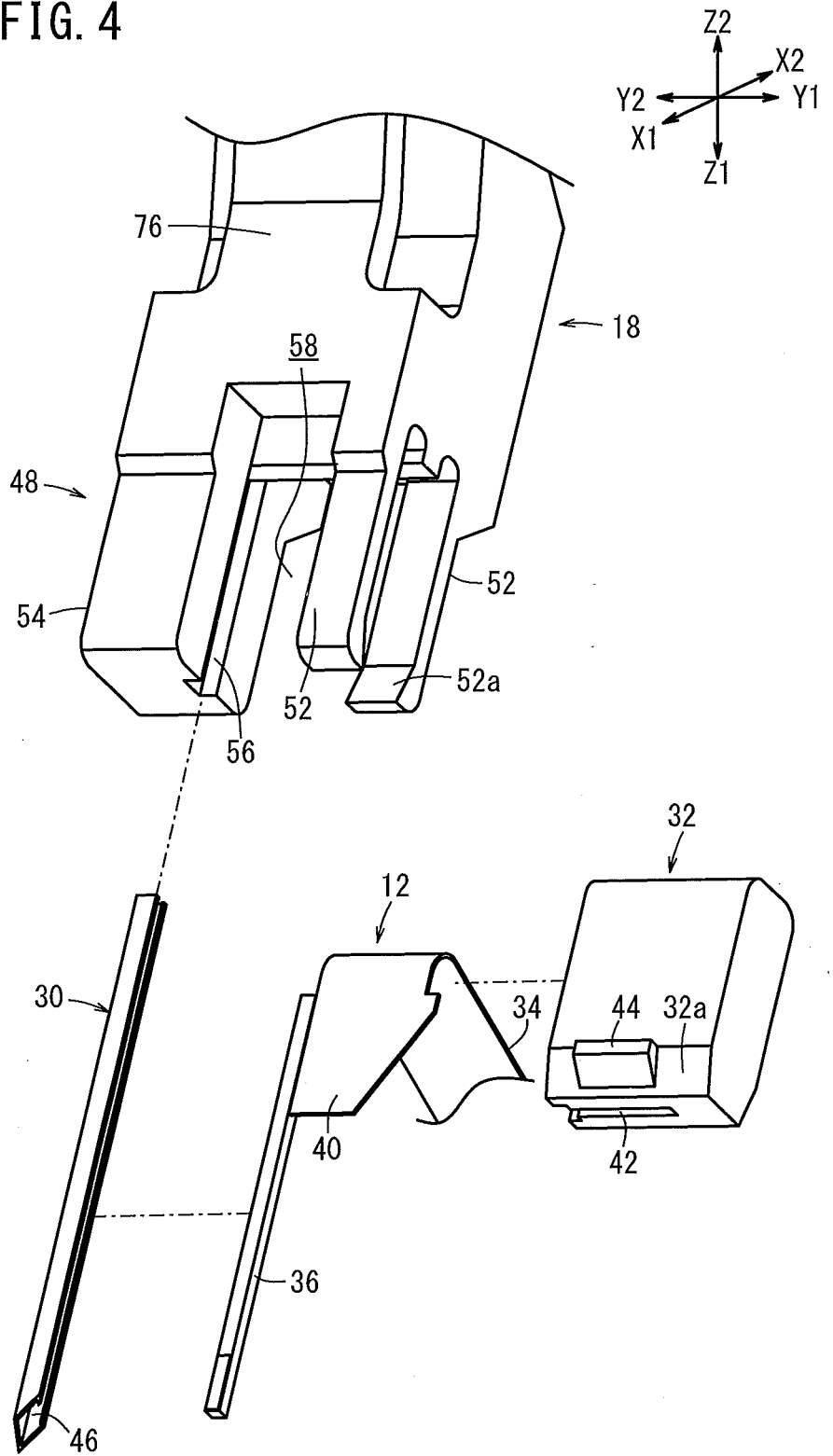

SENSOR INSERTION DEVICE AND METHOD FOR OPERATING SAID DEVICE

CROSS REFERENCE TO RELATED APPLICATIONS

The present application is a continuation-in-part application of and claims the benefits of and priority, under 35 U.S.C. §120, to Patent Cooperation Treaty Application Serial No. PCT/JP2013/054920, filed Feb. 26, 2013, which claims the benefits of and priority to Japanese Patent Application No. 2012-056084, filed Mar. 13, 2012. Each of the aforementioned documents is incorporated herein by this reference in their entirety for all that they teach and for all purposes.

TECHNICAL FIELD

The present invention relates to a sensor inserting device for inserting a detector of a sensor, for measuring biological information of a person, into a body of the person and an operating method of the device.

BACKGROUND

Conventionally, a sensor is inserted or implanted in a body of a person to be measured (patient) to detect an analyte (e.g., glucose or pH, cholesterol, protein, or the like) in blood or a body fluid of the person to be measured by the sensor. In such case, a sensor inserting device is used to penetrate the skin of the person to be measured and to dispose the sensor rapidly and easily (e.g., see JP 2008-506468 W).

The applicator (sensor inserting device) disclosed in JP 2008-506468 W includes a needle (insertion needle) inserted together with a sensor, a plunger assembly (movement mechanism) for moving and piercing with the sensor and the insertion needle, and an attaching unit (indwelling member) allowing the sensor to be placed on the skin of a patient. Further, for example, an electrode unit (signal processor) for transmitting detected information on blood sugar level (biological information) obtained by the sensor to an external medical device is attached to the sensor.

Usually, to insert the sensor and let the sensor be placed in the body of a person to be measured using such type of sensor inserting device, the steps (procedure of using) listed below are performed:

[1] Attaching a sensor to a sensor inserting device;
[2] Releasing a safety mechanism of an insertion needle to allow the insertion needle to move freely;
[3] Positioning the sensor inserting device at a desired location (location of insertion) on a body of a person to be measured, and setting the indwelling member on to the skin of the person to be measured;
[4] Operating the sensor inserting device to insert a detector of the sensor and the insertion needle into the body of the person to be measured;
[5] Removing the insertion needle from the sensor and allow the sensor and the indwelling member to be placed in the body (and on the skin) of the person to be measured;
[6] Separating the sensor inserting device from the person to be measured; and
[7] Connecting a signal processor to a sensor portion exposed on the skin of the person to be measured and allowing the sensor and the signal processor to be placed together in communication.

SUMMARY

Technical Problem

As for the sensor for measuring biological information, problems sometime occur in the detector (response unit) or a circuit constituting the sensor. Some such problems with the sensors are, in a case when the analyte is glucose, the deterioration and the deactivation of a fluorescent material or an enzyme that constitutes the detector and that reacts with glucose, a short circuit, or the like.

However, when a conventional sensor inserting device is used, as described in the steps [1] to [7] above, a sensor and a signal processor are connected after the sensor is inserted into a body of the person to be measured. After connecting the signal processor, the user checks whether any problem exists in the sensor based on a signal transmitted from the signal processor. If there is a problem in the sensor, the user removes the sensor from the body of the person to be measured and then inserts another sensor into the body of the person to be measured. That is, when a conventional sensor inserting device is used, even if the sensor has a problem before use, the sensor has to be inserted at least once, which is an unnecessary invasion into the person to be measured. Further, whether the inserting operation is done correctly cannot be grasped immediately after the inserting operation, which can cause stress to the person being measured.

The embodiments presented herein help solve the problem described above. The object of the embodiments is to provide a sensor inserting device and an operating method of the device. The sensor inserting device allows the operating state of the sensor to be checked in real time before insertion of the sensor, by connecting the signal processor and the sensor, so that unnecessary insertion of a sensor having a problem can be avoided. The sensor inserting device allows the determination of whether the inserting operation of the sensor is done correctly to be grasped immediately. Thus, the embodiments help reduce stress and pain of the person to be measured.

Solution to Problem

To achieve the object mentioned above, the embodiments provide a sensor inserting device for inserting a sensor for measuring biological information of a person. The sensor inserting device includes a device main body, a movement mechanism provided in the device main body and configured to move a detector of the sensor and an insertion needle, with the sensor held together with the insertion needle for piercing the body of the person to be measured in a held state, toward the person to be measured to insert the detector and the insertion needle into the body of the person to be measured, and a signal processor that can be attached to and detached from the device main body and processes a signal including biological information from the sensor. The device main body is provided with a signal transmitting part capable of transmitting a signal between the sensor and the signal processor when the signal processor is attached to the device main body in the held state of the movement mechanism.

Since the sensor inserting device is configured such that the signal processor is attached to the device main body and the signal transmitting part can transmit a signal between the sensor in the held state and the signal processor, the operating state of the sensor can be checked by the signal processor before inserting the detector of the sensor and the insertion needle into the body of the person to be measured. In this manner, if there is a problem (abnormality) in the sensor, the sensor will not be inserted so that the stress and pain of unnecessary insertions are eliminated or mitigated. Further, the sensor having a problem can immediately be replaced with a normal sensor so that working efficiency of insertion and indwelling of the sensor can be improved. Moreover, before and immediately after the insertion operation, the person to be measured can check whether the operation is done correctly through the signal processor by watching for any problem caused by the inserting operation based on a signal transmitted from the signal transmitting part. This modification improves functionality.

In embodiments, an external device (a display unit) or a signal processor provides an alarming unit that determines the operating state of the sensor when the signal processor is attached and informs the user of any problem in the sensor when a circuit including the signal transmitting part connected to the sensor or the sensor itself has a problem.

By including the alarming unit informing the user of any problem in the sensor, the user can easily recognize the problem in the sensor in the sensor inserting device.

The device main body may include an indwelling member placed (set) on the skin of the person to be measured together with the sensor and the signal processor. The indwelling member may include a signal processor attaching unit for attaching the signal processor and a fix-connection unit that fixes one of ends of the signal transmitting part so as to electrically connect the signal processor and the signal transmitting part when the signal processor is attached.

By the indwelling member including the fix-connection unit electrically connecting the signal processor and the signal transmitting part when the signal processor is attached, the signal processor attached to the indwelling member and the sensor can easily be connected via the signal transmitting part.

The signal transmitting part is configured with a flexible object, a linear object having a small diameter, or the like.

Thus, the sensor and the insertion needle can transit from the held state and move into the body of the person to be measured with the connection between the signal processor and the sensor maintained.

Further, the distance from the sensor to the fix-connection unit, in the held state, and the distance from the sensor to the fix-connection unit, in the state in which the detector is inserted in the body of the person, are approximately the same.

In this manner, the length of the signal transmitting part extending from the sensor to the fix-connection unit can suitably be determined. Therefore, a slack of the signal transmitting part between the sensor and the fix-connection unit can be minimized, thereby reducing the portion of the signal transmitting part entering the indwelling member so that the signal transmitting part can easily be contained in the indwelling member.

The indwelling member includes a receiving portion for receiving the signal transmitting part, at the location in the vicinity of where the detector is inserted into the person to be measured.

Having the receiving portion for receiving the signal transmitting part, the receiving portion can receive the signal transmitting part and move together with the sensor. This suppresses vibration of and damage to the signal transmitting part and can prevent the signal transmitting part from coming off from the sensor or the fix-connection unit.

The movement mechanism is a push handle that is contained in the device main body and configured to advance toward the person to be measured to insert the detector and the insertion needle and to retreat away from the person to pull out the insertion needle. The sensor inserting device provides the device main body and the push handle with a retreat preventing mechanism to prevent the push handle from retreating at the distanced position where the insertion needle is separated from the person to be measured.

By including the retreat preventing mechanism to prevent the push handle from retreating, the push handle is prevented from coming out of the device main body.

Further, the sensor inserting device provides the device main body and the push handle with an advance preventing mechanism to prevent the push handle from advancing at the distanced position.

This prevents the push handle, positioned at the distanced position, from advancing, so that the problem of unintentionally advancing the insertion needle to make a piercing can be avoided.

The advance preventing mechanism can be configured with a distal end portion of an elastic piece provided on the push handle and an engagement portion provided on the proximal end of the device main body. The distal end portion of the elastic piece exposes itself from the proximal end of the device main body at the distanced position to engage with the engagement portion, thereby preventing the push handle from advancing.

In this manner, after the sensor is inserted, the sensor inserting device can easily prevent the push handle from advancing by the elastic piece of the push handle engaging with the engagement portion of the device main body.

The movement mechanism is a push handle that is contained in the device main body and configured to advance toward the person to be measured to insert the detector and the insertion needle and to retreat away from the person to be measured to pull out the insertion needle. The sensor inserting device provides the device main body and the push handle with a retaining mechanism that retains the push handle at a retaining position, in which the push handle in the held state is retained to be separated from the distal end portion of the device main body by a predetermined distance, and allows the push handle to advance by operating a controller provided on the push handle.

Configured in such manner, the controller of the retaining mechanism provides a safety function to permit the push handle to advance, which can avoid the problem of unintentionally advancing the push handle in the held state to make piercing.

To achieve the object, the embodiments provide an operating method of the sensor inserting device that holds the sensor and an insertion needle for measuring biological information at the location distanced from the distal end portion of the device main body by a predetermined distance and includes the signal transmitting part, disposed between the sensor and the fix-connection unit of the device main body, for transmitting a signal including biological information output from the sensor. The method includes a connecting step for attaching a signal processor for processing the signal to the device main body to provide continuity between the signal processor and the fix-connection unit so as to allow transmission of the signal between the sensor and the signal processor, an advance motion step, performed after the connecting step, for advancing the sensor and the insertion needle toward the distal end by the movement mechanism provided in the device main body so as to project the detector of the sensor and a portion of the insertion needle from the distal end of the device main body, and a retreat motion step, performed after the advance motion step, for removing the insertion needle from the sensor by retreating the insertion needle toward the proximal end by the movement mechanism.

The method further includes, between the connecting step and the advance motion step, a checking step for detecting the operating state of the sensor and informing the user of, by the alarming unit, any abnormality in the sensor when a circuit including the signal transmitting part connected to the sensor or the sensor itself has a problem.

Advantageous Effects of the Embodiments

In embodiments, the operating state of the sensor can be checked before insertion of the sensor by connecting the signal processor and the sensor so that unnecessary insertion of a sensor having a problem can be avoided, and the inserting operation of the sensor can also be check to determine if the insertion was done correctly, thereby reducing stress and pain of a person to be measured.

BRIEF DESCRIPTION OF THE DRAWINGS

FIG. 4 is an enlarged perspective view illustrating a distal end portion of a push handle illustrated in FIG. 2.

DETAILED DESCRIPTION

Embodiments of a sensor inserting device and an operating method of using the sensor inserting device will be described in detail below with reference to the attached drawings.

Figure 1:
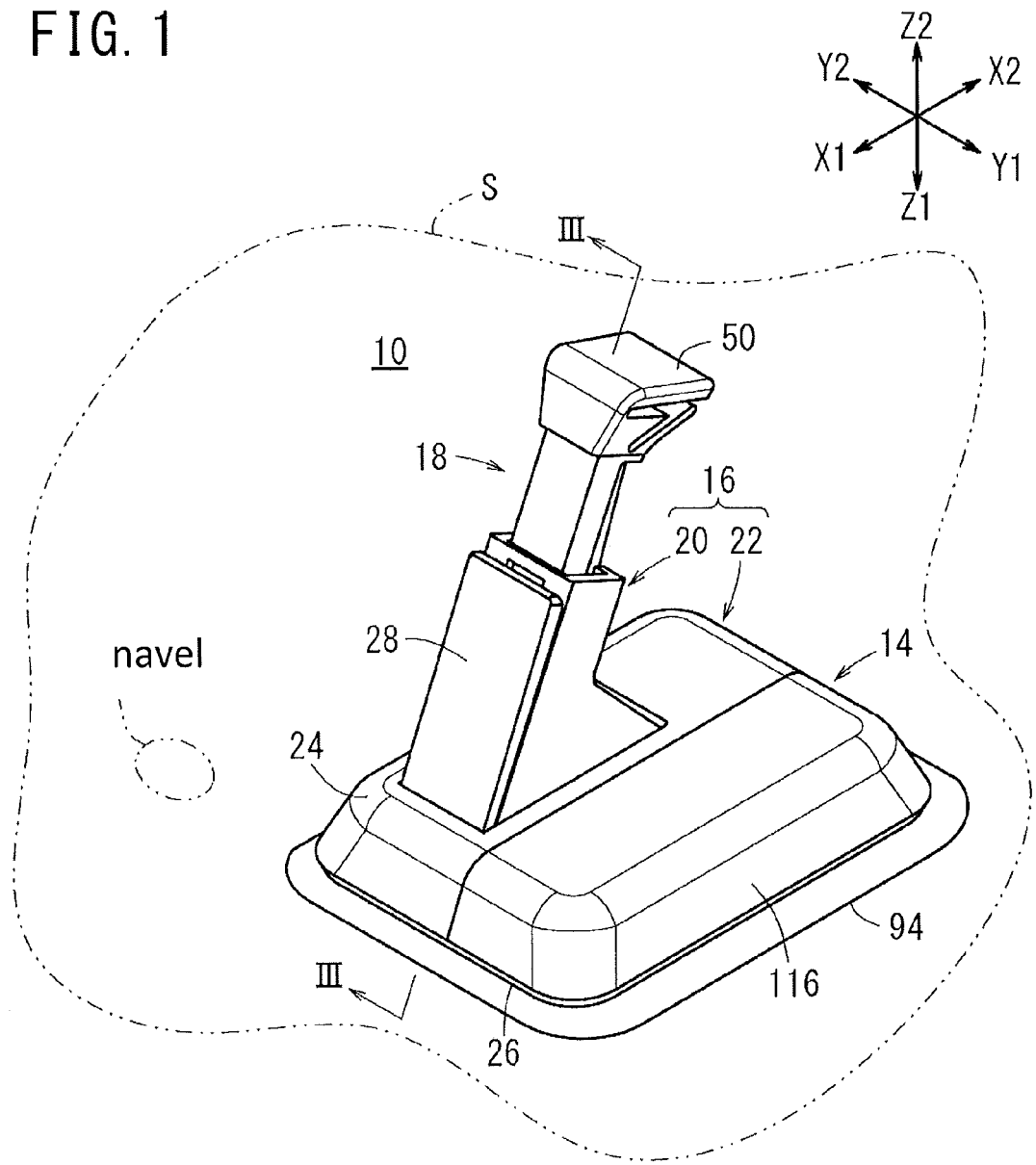
FIG. 1 is a perspective view schematically illustrating a sensor inserting device.
Figure 2:
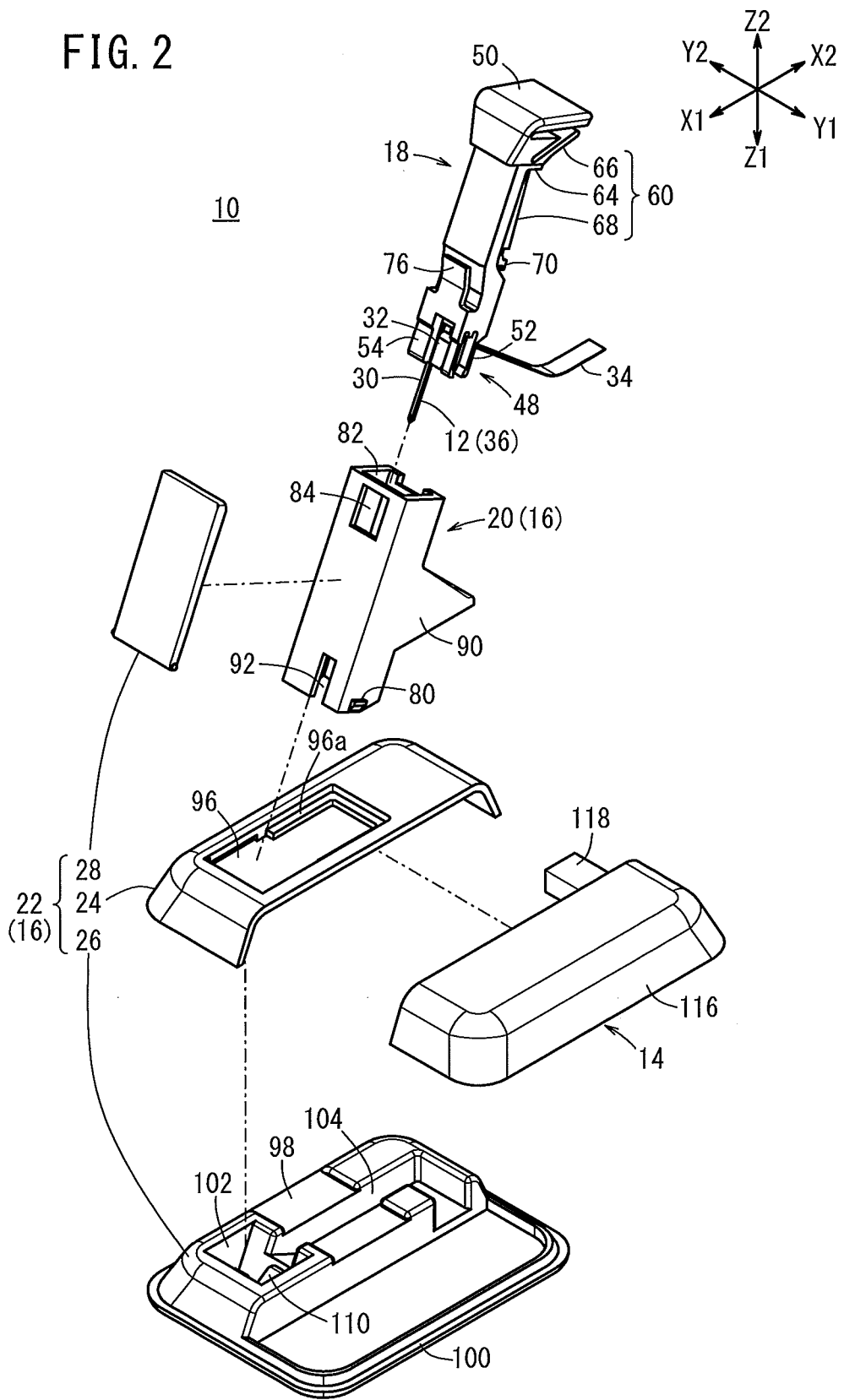
FIG. 2 is an exploded perspective view of the sensor inserting device illustrated in FIG. 1.
Figure 3:
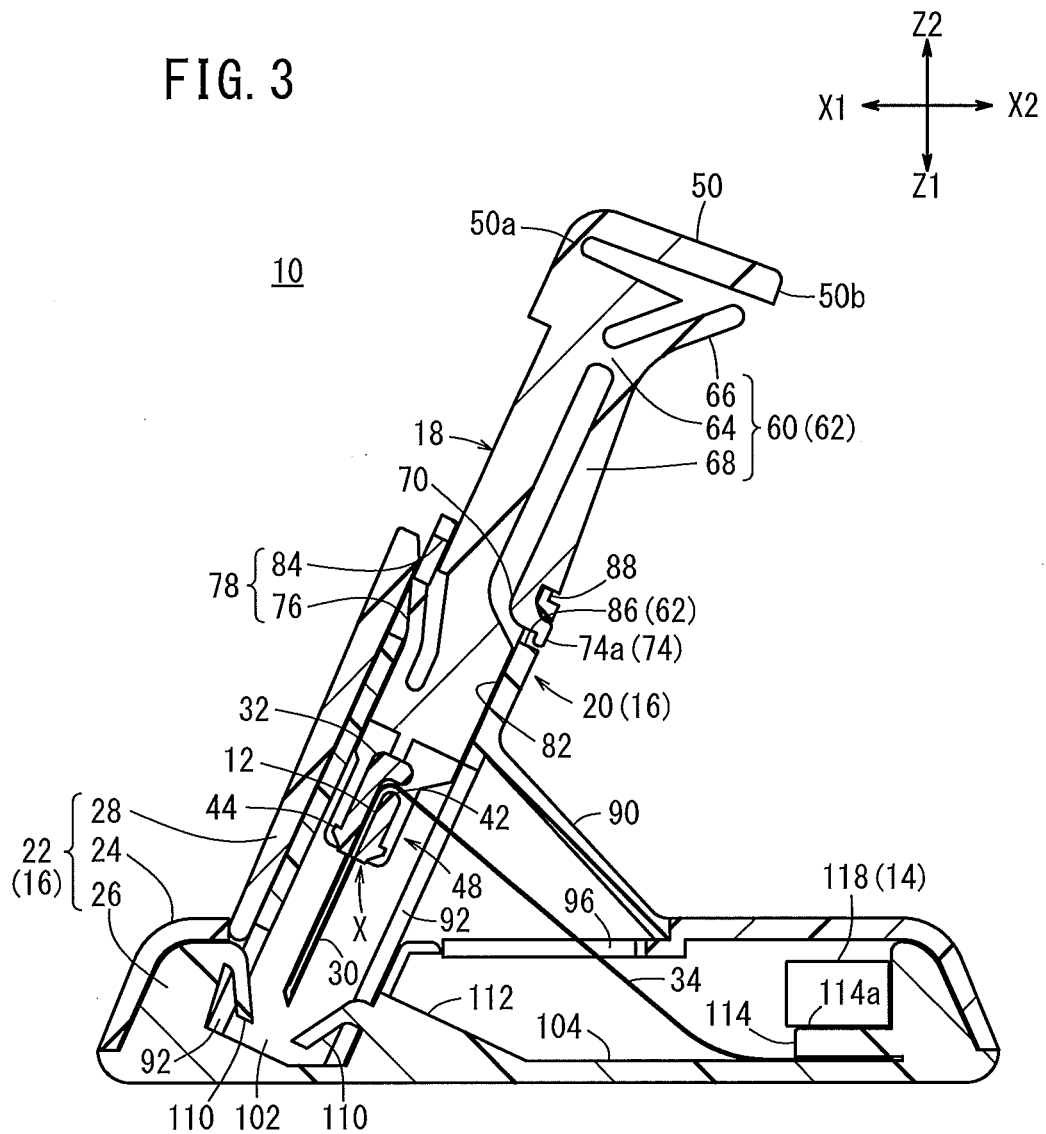
FIG. 3 is a cross sectional view of the sensor inserting device taken along line III-III in FIG. 1.

FIG. 1 is a perspective view schematically illustrating an embodiment of a sensor inserting device 10. FIG. 2 is an exploded perspective view of the sensor inserting device 10 illustrated in FIG. 1. FIG. 3 is a cross sectional view of the sensor inserting device 10 taken along line III-III in FIG. 1. In the description below, according to the illustration of the sensor inserting device 10 in FIG. 1, the front-and-rear direction of the device is referred to as the X direction, the right-and-left direction of the device is referred to as the Y direction, and the height direction of the device is referred to as the Z direction (up-and-down direction). Further, the downward direction of the sensor inserting device 10 is also referred to as the distal end direction or Z1 direction and the upward direction of the sensor inserting device 10 is also referred to as the proximal end direction or Z2 direction. Further, the forward direction and the rearward direction of the sensor inserting device 10 are also referred to as X1 direction and X2 direction, respectively, and the rightward direction and the leftward direction of the sensor inserting device 10 are referred to as Y1 direction and Y2 direction, respectively. These directions are provided for convenience of description. It goes without saying that the sensor inserting device 10 can be used in any direction.

As illustrated in FIG. 1, the sensor inserting device 10 is a device that is disposed at a suitable location (e.g., an unobtrusive portion of a person's body where the body motion is small such as an abdomen, specifically, a location near a navel, etc.) on a skin S of a patient (person to be measured), and may insert a sensor 12 (see FIG. 4) into the body of the patient, by a predetermined operation by a user, to allow the sensor 12 and the transmitter 14 (signal processor) to be placed on the skin S. Not only doctors and nurses, but also a patient is included in the term "user".

The sensor inserting device 10 includes a device main body 16 and a push handle 18 (movement mechanism) that can move relative to the device main body 16. As illustrated in FIG. 2 and FIG. 3, the device main body 16 includes a guide sleeve 20, extending approximately along the up-and-down direction, and an indwelling member 22, provided in the distal end side (Z1 direction) of the guide sleeve 20, sticking on to the skin S of the patient. The indwelling member 22 is configured with an upper case 24, a bottom case 26, and a lid 28. On the bottom case 26, the transmitter 14 can be attached. On the distal end portion of the push handle 18, the insertion needle 30 is attached and the sensor 12 is engaged via a sensor cover 32.

The sensor inserting device 10 is configured such that the sensor 12 and the transmitter 14 are electrically connected via a flexible cable 34 (a signal transmitting part: hereinafter, also referred to as simply a "cable") and physically connected by attaching the transmitter 14 to the indwelling member 22. Further, by operating the components together, the sensor 12 (detector 36) can rapidly and precisely be inserted into the body through the skin S of the patient so as to allow the sensor 12 and the transmitter 14 to be placed on and/or under the skin S of the patient.

The sensor 12, inserted into the body of the patient by the sensor inserting device 10, detects information on glucose concentration (biological information: blood sugar level) included in a body fluid component of the patient. The detected information on glucose concentration is automatically transmitted wirelessly to an external display unit 38 (see FIG. 9) via a transmitter 14 and used for the management of the blood sugar level of the patient. It goes without saying that an object, inserted by the sensor inserting device 10, is not limited to the sensor 12 for detecting the glucose concentration. The device can be used for various applications, for example, for insertion and indwelling of a sensor for detecting biological information such as pH, cholesterol, and protein.

FIG. 4 is an enlarged perspective view illustrating a distal end portion of the push handle 18, illustrated in FIG. 2. As illustrated in FIG. 4, the sensor 12 includes the detector 36, inserted into the body of a patient, to contact the body fluid (blood), and a sensor base part 40, that is held by the sensor cover 32. The sensor base part 40 is located on the skin S of the patient when the detector 36 is inserted into the body of the patient.

A measuring method for measuring glucose concentration in a blood component using the sensor 12 is used. For example, a method using a fluorescent dye (fluorescent material) emitting fluorescent light by coupling with glucose or reacting with fluorescent light may be used. The sensor 12 (detector 36) can be configured according to an analyte component to be measured or a particular, predetermined measuring method. For example, when an enzyme method is used for measuring blood sugar level, a glucose oxidase (GOD) electrode using an enzyme reacting with glucose may be used.

The tubular detector 36 is flexible so that the tubular detector 36 can easily be inserted in the body of the patient, reducing damage to a body tissue. The length of the detector 36 depends on an object in which the detector 36 is inserted (a blood vessel or a living body tissue) and the location of insertion. For example, when the detector 36 is inserted into the abdomen of a patient, the length is set to be 0.2 to 10 mm.

The sensor base part 40 is formed in a thin plate shape and connected to the proximal end side of the detector 36. The sensor base part 40 is covered with an insulation material. A sensor circuit, which is not shown in the drawing, is provided inside the sensor base part 40. For example, the sensor circuit using a fluorescent dye has a structure in which a base made of silicon or the like, a light-receiving element, a protection layer, a filter, a light emitting element, an indicator layer, and the like are laminated onto the sensor base part. The detector 36 is connected to the indicator layer.

In the proximal end side (Z2 direction) of the sensor base part 40, a cable 34 is electrically connected to the sensor circuit. The sensor 12 is configured such that the sensor base part 40 is held by the sensor cover 32 so that the detector 36 extends from the distal end side of the sensor cover 32. The sensor 12 is held in this state in the push handle 18 (see FIG. 3).

The sensor cover 32 has sufficient thickness to hold the sensor base part 40 from both sides of the sensor base part 40. The sensor cover 32 holds the sensor 12 and also protects the sensor circuit by covering the front and rear faces (both side faces in the X direction) of the sensor base part 40. On the side face, in the Y direction, of the sensor cover 32, a slit 42 for inserting therein the sensor base part 40 is formed. As illustrated in FIG. 3, the slit 42 penetrates the distal end face of the sensor cover 32 and bends at a predetermined location to penetrate the back face (side face in the X2 direction) of the sensor cover 32. From the slit 42 in the back face, the cable 34 may be attached to the sensor 12.

A tapered face 32a is formed on the distal end portion (in the Z1 direction) of the sensor cover 32 so the thickness of the distal end portion decreases toward the distal end. On the front and rear faces of the distal end portion, a pair of protrusions 44 are formed. By the pair of protrusions 44 engaging with hooks 110 (see FIG. 3) of the indwelling member 22 when the sensor 12 is inserted, the sensor 12 and the sensor cover 32 engages with the indwelling member 22.

The sensor inserting device 10 is configured to hold the sensor 12 inside the device main body 16 by the sensor cover 32 engaging with the distal end portion of the push handle 18. In this configuration, the insertion needle 30 is also attached to the distal end portion of the push handle 18. The insertion needle 30 is configured of a rigid metal material (e.g., a stainless steel) so as to easily pierce the skin S of the patient.

The distal end portion of the insertion needle 30 is partially cut to have an acute angle (i.e., the needle is sharp or sharpened) so as to easily pierce the skin S. The insertion needle 30 is formed to have a U-shaped (or C-shaped) cross section opening in the Y1 direction. The inside of the U-shape forms an insertion needle side groove 46. The insertion needle side groove 46 extends along the axial direction and can contain the detector 36 of the sensor 12. That is, the sensor 12 is held at the distal end portion of the push handle 18 with the sensor base part 40 covered by the sensor cover 32 and the detector 36 covered by the insertion needle 30.

Figure 5A:
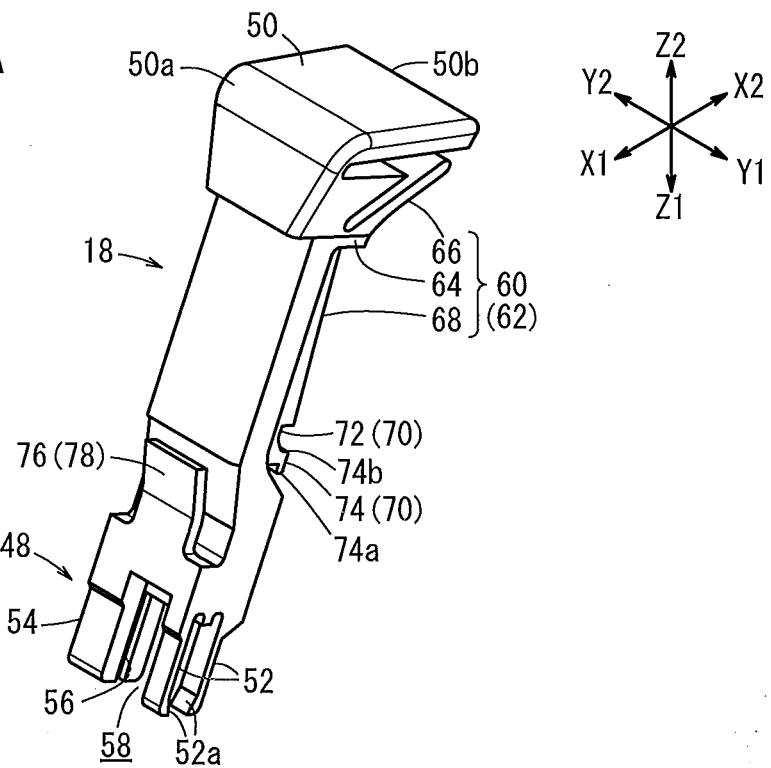
FIG. 5A is an enlarged perspective view illustrating the push handle illustrated in FIG. 1.
Figure 5B:
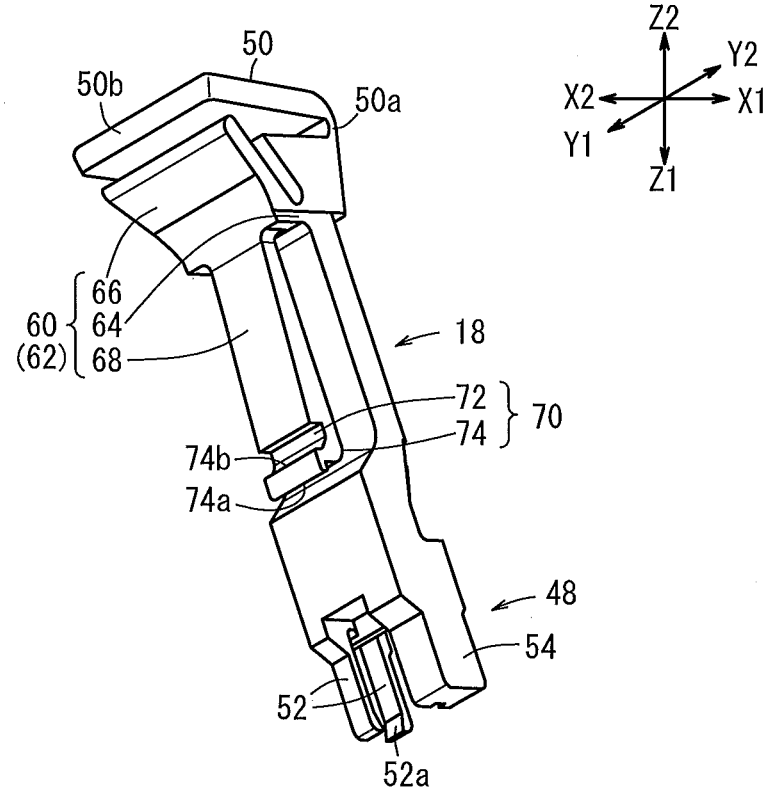
FIG. 5B is a perspective view illustrating the push handle illustrated in FIG. 5A viewed from the opposite side.

FIG. 5A is an enlarged perspective view illustrating the push handle 18 illustrated in FIG. 1. FIG. 5B is a perspective view illustrating the push handle 18 illustrated in FIG. 5A viewed from the opposite side. The push handle 18 is formed as a column-shaped member extending in the up-and-down direction and inserted in the guide sleeve 20 of the device main body 16. As illustrated in FIG. 5A and FIG. 5B, a holding portion 48 for holding the sensor 12 and the insertion needle 30 described above is provided at the distal end portion (bottom portion) of the push handle 18. Further, a controller 50 for pushing the push handle 18 toward the distal end is formed on the proximal end portion (top portion) of the push handle 18.

As illustrated in FIG. 4, the holding portion 48 includes a pair of legs 52, protruding toward the distal end in the Y1 direction side, and a protruding portion 54 that is formed thicker than the leg 52, protruding toward the distal end in the Y2 direction side. The pair of legs 52 extends longer than the length of the sensor cover 32 in the up-and-down direction and is configured to hold the sensor cover from both sides. Tapered faces 52a opposing each other are formed on the distal end portions of the pair of legs 52 so as to make contact with the tapered faces 32a of the sensor cover 32. In this manner, the pair of legs 52 holds the sensor cover 32 with a suitable engaging force to prevent the sensor cover 32 from coming off.

The protruding portion 54 is provided to be separated in the width direction from the pair of legs 52 by a predetermined distance and protrudes toward the distal end so as to support the side face, in the Y2 direction, of the sensor cover 32. On the side face, in the Y1 direction, of the protruding portion 54, a push handle side groove 56 is formed by grooving the side face in the axial direction. The push handle side groove 56 engages with the insertion needle 30 along the axial direction to firmly hold the insertion needle 30, preventing the insertion needle 30 from coming off along the axial direction.

Between the pair of legs 52 and the protruding portion 54 of the holding portion 48, that is, in the middle of the width direction, a space 58 is formed. The sensor cover 32 is held in the holding portion 48 by the pair of legs 52 from both sides so as the protrusions 44 to be positioned within the space 58. Further, the cable 34 extending from the back face of the sensor cover 32 straightly extends through the space 58 toward the indwelling member 22.

As illustrated in FIG. 5A and FIG. 5B, the controller 50 is configured as a rectangular elastic piece. At the proximal end of the push handle 18, only one side in the X1 direction is connected to the column-shaped main body. In this manner, the end portion, in the X2 direction side, of the controller 50 (hereinafter referred to as a pusher end 50*b*) is movable in the up-and-down direction about a connecting portion 50*a*. The controller 50 is used to push a rotary-engagement-portion 60 provided in the lower side by the downward movement of the pusher end 50*b*.

The rotary-engagement-portion 60 is provided in the X2 direction side of the push handle 18 and extends from the upper portion to the middle portion of the push handle 18. The rotary-engagement-portion 60 constitutes a portion of the retaining mechanism 62 for holding the push handle 18 at a predetermined relative height to the guide sleeve 20. The retaining mechanism 62 restricts the push handle 18 from unintentionally moving (advancing) toward the distal end.

In the rotary-engagement-portion 60, a fulcrum 64, an upper extending piece 66 extending diagonally upward from the fulcrum 64, and a lower extending piece 68 extending downward from the fulcrum 64 are integrally formed. The fulcrum 64 elastically supports the upper extending piece 66 and the lower extending piece 68. When the push handle 18 is inserted in the guide sleeve 20, the fulcrum 64 urges the distal end portion of the lower extending piece 68 toward the X2 direction.

The upper extending piece 66 extends further enough to oppose the bottom face of the pusher end 50*b* of the controller 50. Therefore, when the pusher end 50*b* is pushed downward, the bottom face of the pusher end 50*b* contacts the upper extending piece 66 and the pushing force is transmitted to the rotary-engagement-portion 60. In this manner, the rotary-engagement-portion 60 makes the upper extending piece 66 and the lower extending piece 68 rotate together about the fulcrum 64.

On the distal end portion of the lower extending piece 68, a hooking portion 70 that can engage with a retaining hole 86 (see FIG. 3) of the guide sleeve 20 is provided. The hooking portion 70 includes a concave portion 72 facing the X2 direction and a hooking latch 74 that curves along the concave portion 72 and protrudes toward the distal end. The hooking latch 74 includes, on the distal end portion thereof, a projecting portion 74*a*. A curved face 74*b* is formed on the edge in the proximal end side of the hooking latch 74. The retaining mechanism 62 holds the push handle 18 at a predetermined height in the device main body 16 by the hooking latch 74 being engagingly inserted in the retaining hole 86. In the state when the hooking latch 74 is engaged in the retaining hole 86, the top end portion of the guide sleeve 20 enters into the concave portion 72 to securely engage the hooking latch 74 with the guide sleeve 20.

The rotary-engagement-portion 60 rotates the lower extending piece 68 when the upper extending piece 66 is pushed by the controller 50, and thereby removes the hooking latch 74 out of the retaining hole 86. In this manner, the held state of the push handle 18 in the guide sleeve 20 is released so that the push handle 18 can advance toward the distal end of the guide sleeve 20.

On the top portion of the holding portion 48 of the push handle 18, an anti-separation piece 76 diagonally extending upward is provided. Operating together with a restriction hole 84 of the guide sleeve 20 (see FIG. 3), the anti-separation piece 76 constitutes a portion of the retreat preventing mechanism 78 that prevents the push handle 18 from coming out of the guide sleeve 20. That is, when the push handle 18 makes a retreat motion toward the proximal end, the retreat motion is restricted by the anti-separation piece 76 entering into the restriction hole 84, thereby preventing the push handle 18 from coming off the guide sleeve 20. In the held state of the push handle 18, the anti-separation piece 76 partially enters into the restriction hole 84 and a plane face of the anti-separation piece 76 engages with the lip of the restriction hole 84. In this manner, the force holding the push handle 18 can be enhanced.

Figure 6A:
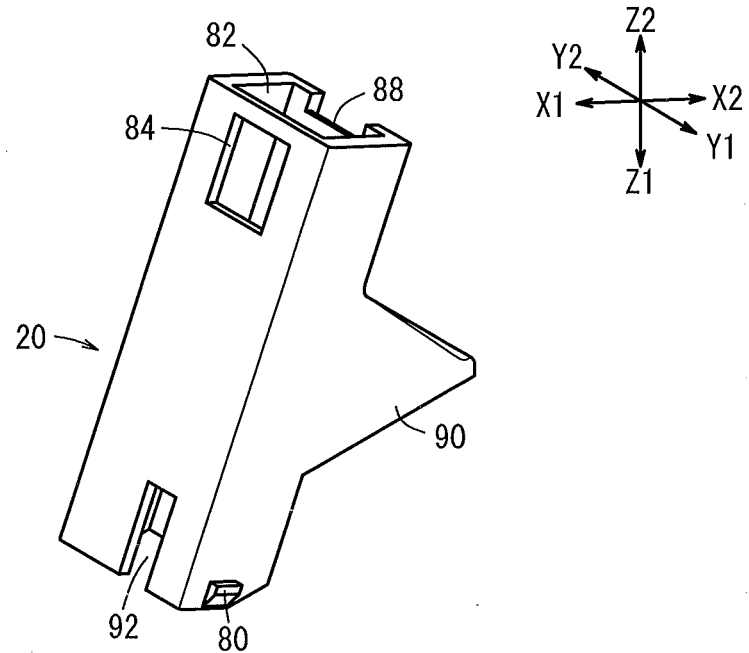
FIG. 6A is an enlarged perspective view illustrating a guide sleeve illustrated in FIG. 1.
Figure 6B:
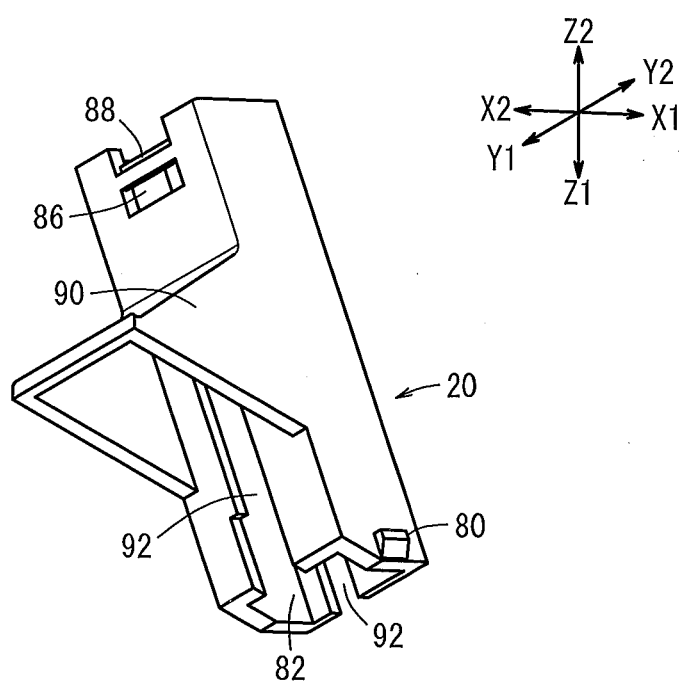
FIG. 6B is a perspective view illustrating the guide sleeve illustrated in FIG. 6A viewed from the opposite side.

FIG. 6A is an enlarged perspective view illustrating a guide sleeve 20 illustrated in FIG. 1. FIG. 6B is a perspective view illustrating the guide sleeve 20 illustrated in FIG. 6A viewed from the opposite side. As illustrated in FIG. 6A and FIG. 6B, the guide sleeve 20 is formed in a rectangular sleeve shape and diagonally attached to the indwelling member 22 with a predetermined angle. For example, the predetermined angle is any angle from 60° to 90°, but is preferably from 60° to 70° degrees. On the distal end portion of the guide sleeve 20, a pair of distal end projecting portions 80 engaging with the indwelling member 22 is provided. Further, a guide hole 82 is formed to penetrate, in the axial direction, the inside of the guide sleeve 20. The push handle 18 is guided along the guide hole 82 when advancing toward the distal end and retreating toward the proximal end.

On the side face, in the X1 direction in the proximal end side of the guide sleeve 20, the elongated restriction hole 84, elongated in the axial direction, is formed. As described above, the restriction hole 84 operates together with the anti-separation piece 76, of the push handle 18, to restrict the retreat motion of the push handle 18.

On the side face, in the X2 direction of the proximal end side of the guide sleeve 20, the retaining hole 86 is formed. As described above, the retaining hole 86 engages with the hooking latch 74 of the push handle 18 when the hooking latch 74 is inserted in the retaining hole 86, thereby keeping the push handle 18 at the predetermined height. Note that, the upper side of the lip composing the retaining hole 86 is formed to have a curved shape so that the curved face 74*b* of the hooking latch 74 can easily go over the upper side of the lip when the push handle 18 retreats.

Further, on the top face of the proximal end, in the X2 direction of the guide sleeve 20, a notch 88 constituting a portion of the advance preventing mechanism 79 is formed in the width direction. The notch 88 engages with the projecting portion 74*a* of the push handle 18 when the push handle 18 retreats to the location where the anti-separation piece 76 engages with the restriction hole 84 (at the distanced position) (also see FIG. 12). In this manner, the push handle 18 is prevented from advancing again. That is, the advance preventing mechanism 79 prevents the push handle 18 from coming off when the push handle 18 retreats to the distanced position where the insertion needle 30 is separated from the patient, and also prevents the push handle 18 from advancing.

In the lower side of the retaining hole 86 of the guide sleeve 20, a pair of support plates 90 each formed in an approximately triangular shape is provided. A bottom side of the support plate 90 contacts the indwelling member 22 when the guide sleeve 20 is disposed on the indwelling member 22. In this manner, the tilt angle of the guide sleeve 20 to the indwelling member 22 is kept constant.

On both the front and rear (X direction) sides of the distal end portion of the guide sleeve 20, distal end slits 92 cut along the axial direction are formed. The distal end slit 92 in the X1 direction is cut short, and the distal end slit 92 in the X2 direction is cut long so as to reach into the support plate 90 to allow the cable 34 to pass through the distal end slit 92. When the guide sleeve 20 is disposed on the indwelling member 22, a hook 110 (see FIG. 3) of the bottom case 26 is inserted in each distal end slit 92.

Figure 7A:
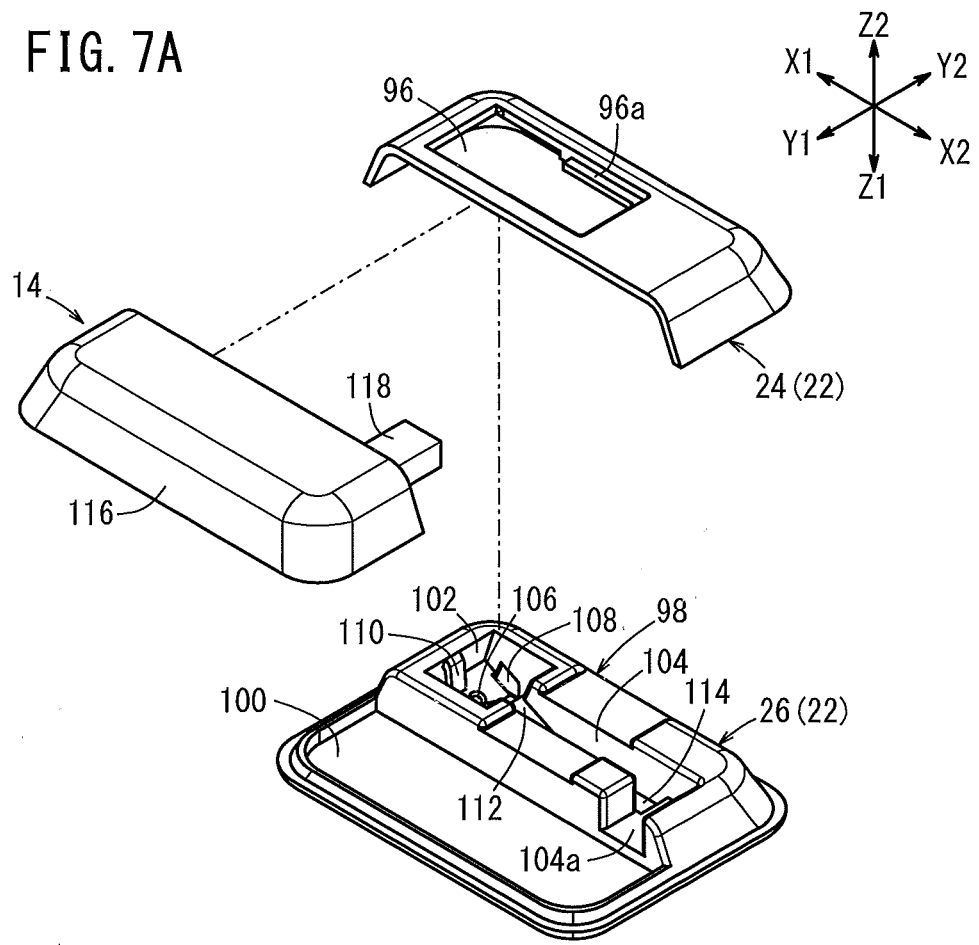
FIG. 7A is an enlarged perspective view illustrating an indwelling member and a transmitter illustrated in FIG. 1.
Figure 7B:
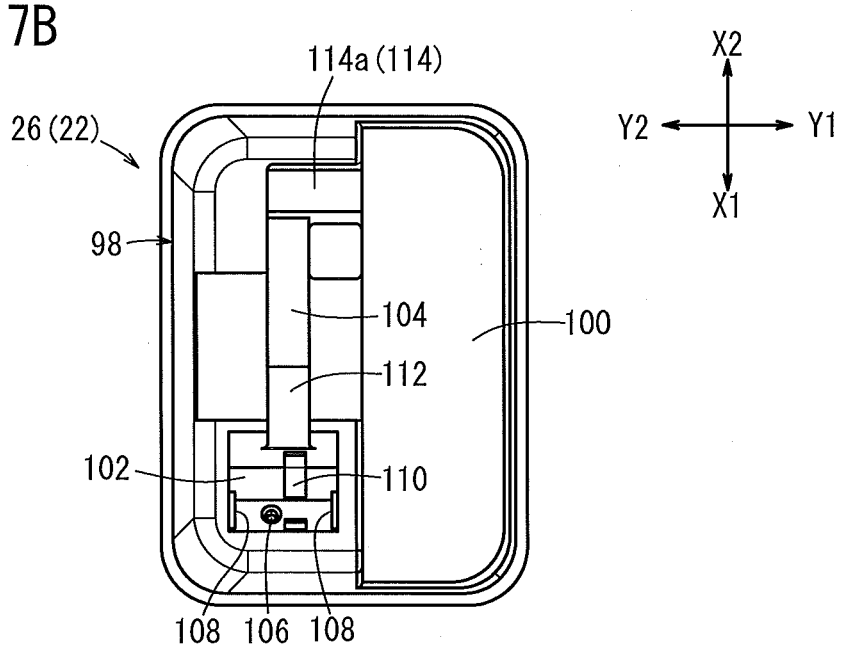
FIG. 7B is a plan view of a bottom case illustrated in FIG. 7A.
Figure 8:
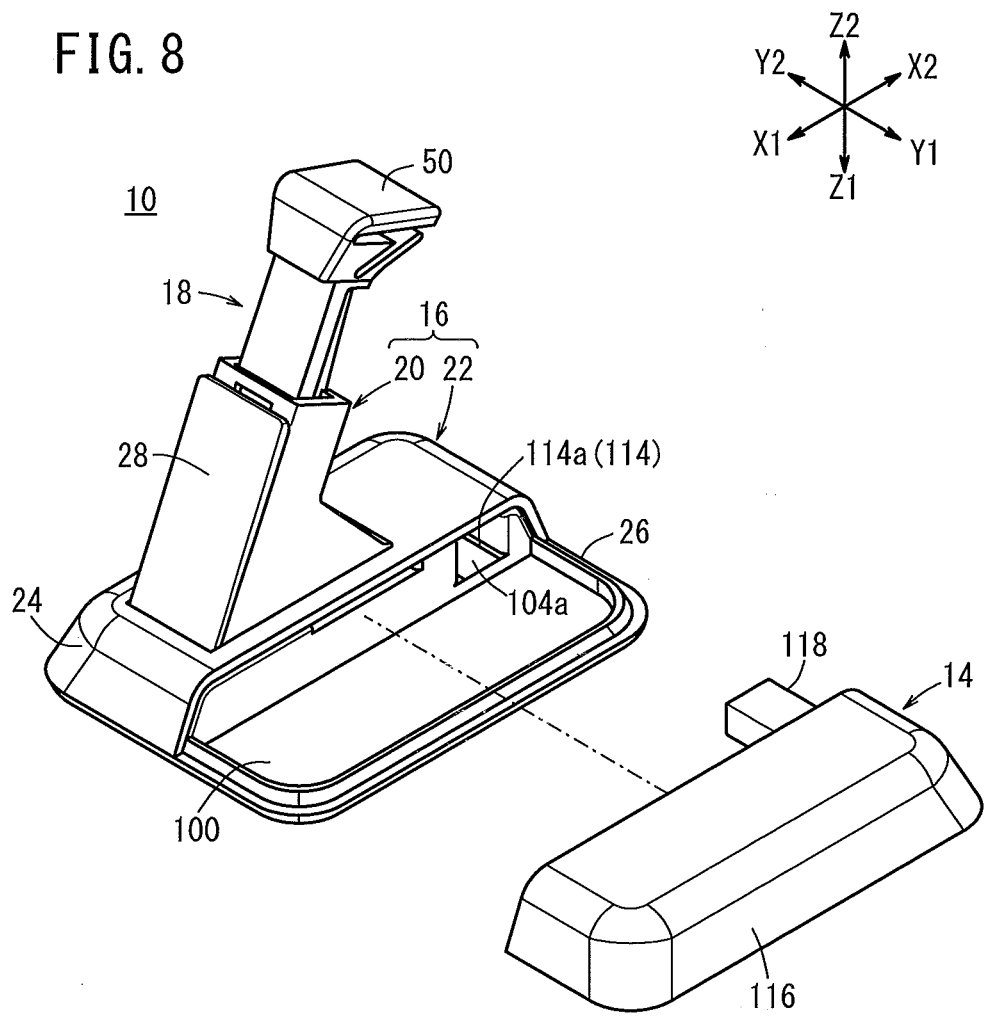
FIG. 8 is an explanatory drawing illustrating a state when the transmitter is disposed in the indwelling member.
Figure 9:
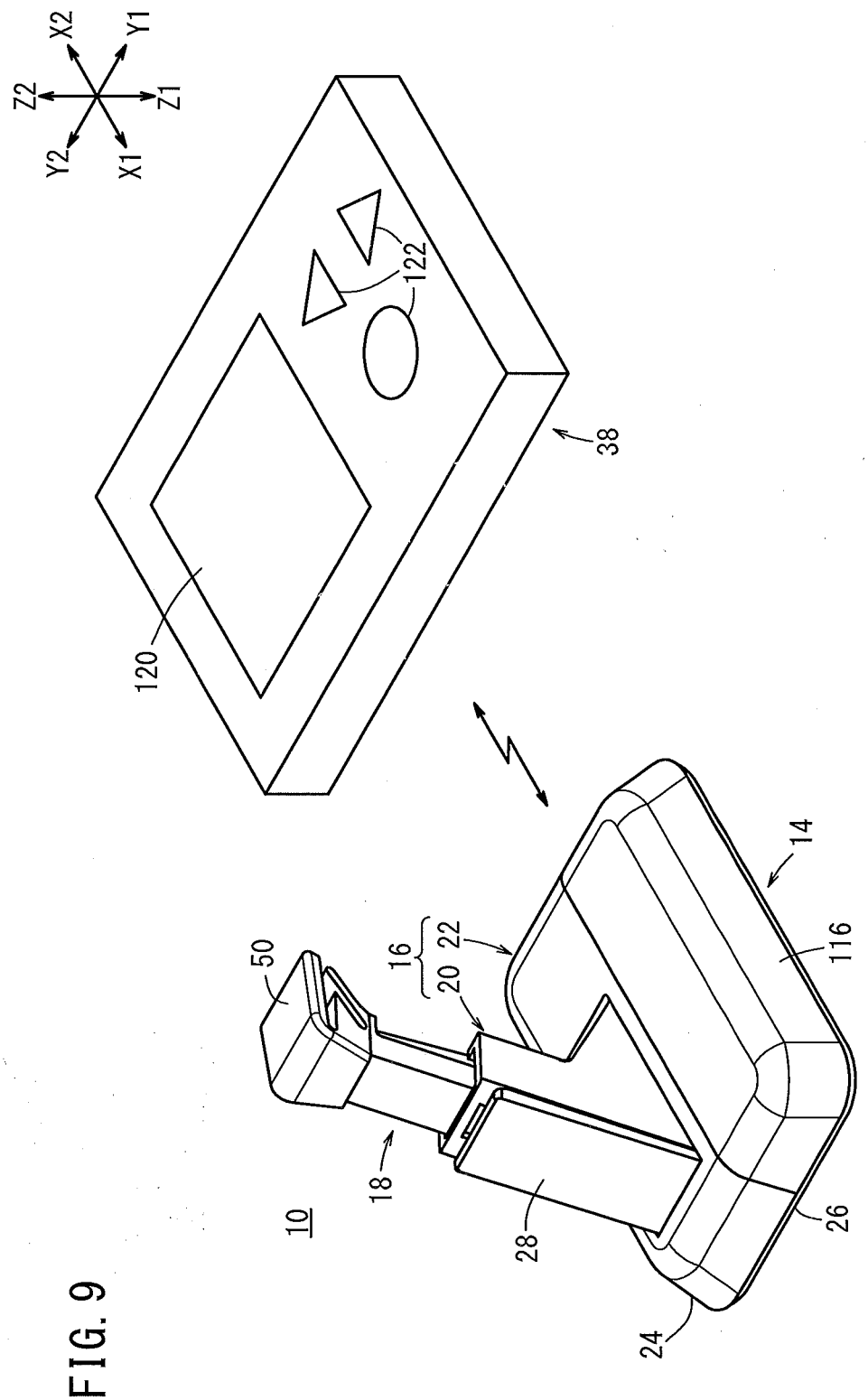
FIG. 9 is an explanatory drawing illustrating the relationship between the sensor inserting device, with the transmitter attached thereto, and a display unit.

FIG. 7A is an enlarged perspective view illustrating the indwelling member 22 and the transmitter 14 illustrated in FIG. 1. FIG. 7B is a plan view of the bottom case 26 illustrated in FIG. 7A. FIG. 8 is an explanatory drawing illustrating a state when the transmitter 14 is disposed in the indwelling member 22. FIG. 9 is an explanatory drawing illustrating the relationship between the sensor inserting device 10, with the transmitter 14 attached thereto, and a display unit 38.

The indwelling member 22, with the distal end portion of the guide sleeve 20 inserted therein, is positioned on the skin S of the patient. The bottom face of the indwelling member 22 is formed flat so as that the indwelling member 22 can easily be positioned on the skin S of the patient. An adhesive sheet 94 (see FIG. 1) for holding the indwelling member 22 on the skin S is attached to the bottom face of the indwelling member 22. When the transmitter 14 is attached to the indwelling member 22, the indwelling member 22 together with the transmitter 14 forms an approximately trapezoidal shape (see FIG. 9). When the transmitter 14 is not attached, the indwelling member 22 has a form in which about a half of the portion in the Y1 direction is cut away (see FIG. 8).

As illustrated in FIG. 7A and FIG. 7B, the upper case 24 is configured to cover about the half of the top face in the Y2 direction of the indwelling member 22. On the top face, from the middle to the X1 direction side, of the upper case 24, an elongated insertion window 96 is drilled. The distal end of the guide sleeve 20 is inserted through the insertion window 96. On the inner side, on the portion in the X2 direction side of the aperture of the insertion window 96, an arrangement projection 96a is formed and protrudes. When the guide sleeve 20 is attached to the indwelling member 22, the arrangement projection 96a contacts the support plate 90 to support the guide sleeve 20.

Further, the lid 28 illustrated in FIG. 2 is rotatably attached to the insertion window 96. When the guide sleeve 20 is removed from the indwelling member 22, the lid 28 closes the insertion window 96. In this manner, intrusion of dust or the like into the indwelling member 22 can be prevented.

The bottom case 26 includes a guide sleeve connector 98 of which portion in the Y2 direction side is formed in a trapezoidal shape. To the side face of the guide sleeve connector 98, a base plate 100 (signal processor arrangement portion) extending in the Y1 direction is connected. The base plate 100 is formed in a thin plate shape that is approximately same as the shape of the bottom face of the transmitter 14 in a plan view (a rectangular shape having round corners). The transmitter 14 is disposed on the top face of the base plate 100.

The guide sleeve connector 98 includes an insertion hole 102 formed at the location where the insertion hole 102 communicates with the insertion window 96 of the upper case 24 and a trench-like container passage 104 that is connected to, and communicates with, the insertion hole 102 and extends in the X2 direction. At a predetermined location on the bottom face of the insertion hole 102, a penetration hole 106, penetrating the distal end side of the bottom case 26, is drilled. The insertion needle 30 (including the detector 36) that advances toward the distal end along with the advance motion of the push handle 18 is inserted through the penetration hole 106. On both sides in the Y direction of the insertion hole 102, a pair of internal projecting portions 108 that engages with the distal end projecting portion 80 of the guide sleeve 20 to temporarily engage with the guide sleeve 20 is provided.

On both sides in the X direction of the insertion hole 102, a pair of hooks 110 is provided (also see FIG. 3). The hook 110 engages with the protrusion 44 of the sensor cover 32 that has advanced toward the distal end along with the advance motion of the push handle 18. The hook 110 engages with the sensor cover 32 so as the sensor cover 32 does not retreat, together with the push handle 18, toward the proximal end. In this manner, the sensor cover 32 including the sensor 12 is retained in the indwelling member 22.

The container passage 104 that is connected to, and communicates with, the insertion hole 102 has the width in the Y direction wider than that of the cable 34 so as to contain the cable 34, as the sensor 12 moves toward the distal end.

On the bottom, in the insertion hole 102 side (i.e., in the vicinity of the sensor 12 that has moved to the distal end side), of the container passage 104, a tapered receiving portion 112 is formed. The receiving portion 112 receives the cable 34, that advances together with the sensor 12, along the tapered surface, thereby preventing electric contact failure between the sensor 12 and the cable 34 (or between the cable 34 and the fix-connection unit 114) by suppressing vibration of the cable 34 in the up-and-down direction.

On the end portion in the X2 direction side of the container passage 104, the fix-connection unit 114, to which one of end portions of the cable 34 is connected, is provided. As illustrated in FIG. 3, the fix-connection unit 114 is formed to have a step in the container passage 104. One of the end portions of the cable 34 is inserted underneath the step and clamped, thereby fixing the cable 34. As illustrated in FIG. 7B, an electrically conductive metal terminal 114a is exposed on the top face of the step. A terminal 118 of the transmitter 14 is disposed so as to make contact with the metal terminal 114a. In this manner, the fix-connection unit 114 surely fixes the cable 34 and also electrically connects the cable 34 and the transmitter 14.

As illustrated in FIG. 3, when the push handle 18, the guide sleeve 20, and the indwelling member 22 are assembled, the distal end portion of the guide sleeve 20 is inserted in the insertion hole 102 of the bottom case 26 through the insertion window 96 of the upper case 24. The guide sleeve 20 and the indwelling member 22 engage with each other by the distal end projecting portion 80 (see FIG. 2) engaging with the internal projecting portion 108 (see FIG. 7A). In this state, the guide sleeve 20 extends in the up-and-down direction with a predetermined tilt angle to the indwelling member 22 by one of sides of the support plate 90 supported by the arrangement projection 96a of the insertion window 96. The hook 110 of the bottom case 26 enters into the distal end slit 92 of the guide sleeve 20.

When the push handle 18 is inserted into the guide hole 82 of the guide sleeve 20, the hooking latch 74 engages with the retaining hole 86 in the upper side of the guide sleeve 20 and the portion of the anti-separation piece 76 is inserted in the restriction hole 84. In this manner, the held state of the push handle 18 is made by the retaining mechanism 62, thereby preventing the push handle 18 from advancing toward the distal end.

As for the sensor 12, with the cable 34 attached thereto, the sensor base part 40 is inserted and held in the slit 42 of the sensor cover 32 and the detector 36 is contained in the insertion needle 30 (insertion needle side groove 46) (also see FIG. 4). By the pair of legs 52 of the push handle 18 holding the portion, in the Y1 direction side, of the sensor cover 32 from both sides, and by the insertion needle 30 engaging with the push handle side groove 56 of the protruding portion 54, the sensor 12 and the insertion needle 30 are held in the holding portion 48 of the push handle 18. In this manner, the sensor 12 and the insertion needle 30 are in a stand-by state at the retaining position X, distanced from the distal end face of the indwelling member 22 by a predetermined distance.

From the sensor base part 40, the cable 34 extends throughout the slit 42 in the back face side of the sensor cover 32, the space 58 of the push handle 18, the distal end slit 92 of the guide sleeve 20, the insertion window 96 of the upper case 24, the container passage 104 of the bottom case 26, and the fix-connection unit 114 formed in the container passage 104, and is fixed by the fix-connection unit 114. The length of the cable 34 is provided so as the slack of the cable 34 to be small between the sensor 12 and the fix-connection unit 114. The fix-connection unit 114 is located so that the angle between the cable 34 extending toward the sensor 12 at the retaining position X and the bottom face of the container passage 104 is 50 degrees or less. This angle suppresses the rotating motion of the cable 34 during insertion of the sensor 12 to be small and prevents the cable 34 from coming off from the sensor 12 or the fix-connection unit 114 when the sensor 12 moves to be inserted.

The cable 34 may have any configuration allowing insertion of the sensor 12 into the body of the patient, while maintaining an electrical connection between and/or with the sensor 12 and/or the transmitter 14. For example, a flexible material (flexible cable), an electric wire having a small diameter, or the like can be used.

The transmitter 14 can be attached to the sensor inserting device 10. As illustrated in FIG. 7A, the transmitter 14 includes an approximately rectangular-shaped case 116 disposed and held on the base plate 100. Inside the case 116 of the transmitter 14, an electric (electronic) circuit structure (not shown in the drawing) for processing blood sugar level (electric current) detected by the sensor 12 (detector 36) is provided. Components of the circuit structure include a current-voltage converter for converting a current value detected by the detector 36 of the sensor 12 into a voltage value, an amplifier for amplifying the voltage value, a transmitting unit for transmitting the voltage value (signal value) wirelessly (or by a wire) to an external device (display unit 38), a battery for supplying power to the sensor 12 and to other devices, and a circuit substrate to which each device is electrically connected. It goes without saying that the circuit structure may have various configurations. For example, a microcomputer or the like for performing processing of a signal value may be implemented in the circuit substrate.

On the predetermined location (in the X2 direction side) on the side surface in the Y2 direction of the transmitter 14, the terminal 118, which can be electrically connected to the fix-connection unit 114 and is in continuity with the internal circuit structure, is provided. As illustrated in FIG. 8, the terminal 118 is inserted in the aperture 104*a* of the container passage 104 formed in the side face, in the Y1 direction, of the guide sleeve connector 98, and the terminal 118 is electrically connected to the metal terminal 114*a*.

As illustrated in FIG. 9, when the transmitter 14 is connected to the indwelling member 22, the sensor inserting device 10 can determine the operating state of the sensor 12 by information wirelessly transmitted by the transmitter 14 and received by the display unit 38 (alarming unit). As described above, the sensor 12 might have a fault (e.g., insufficient sensitivity or false connection in the circuit) in the detector 36 or the sensor circuit (including the cable 34), which hinders correct detection of blood sugar level. Therefore, the user determines, when the transmitter 14 is connected, the operating state of the sensor 12, that is, whether the sensor 12 is operating normally or abnormally (having malfunction) can be determined.

The operating state of the sensor 12 can be determined based on a signal from the sensor 12 electrically connected to the transmitter 14. Usually, the sensor 12 electrically reacts when power is supplied from the transmitter 14, even when the sensor is not detecting blood sugar level. So that, for example, if values of received signals are the same before and after connecting the transmitter 14, it can be determined that there is a short circuit or an open circuit (a break) in the wiring between the sensor 12 and the transmitter 14 (e.g., a sensor circuit). Further, by distinguishing whether the signal transmitted from the transmitter 14 exceeds the threshold value that is previously set for the normal state of the sensor 12 before insertion, an abnormality of the detector 36 (e.g., insufficient sensitivity) can be determined.

As the display unit 38 for displaying (alarming) the operating state of the sensor 12, a device that can perform wireless communication with the transmitter 14 may be used. For example, a terminal for displaying blood sugar level can be used. In this case, the display unit 38 is configured as a portable terminal provided with a display panel 120 and a manipulating button 122. By manipulating the manipulating button 122, the operating state (normal or abnormal) of the sensor 12 is displayed on the display panel 120. Thereby, the user can easily recognize the operating state of the sensor 12.

It goes without saying that the way to give alarm of malfunction of the sensor 12 is not limited to displaying on the display unit 38. For example, an LED configured to emit light (or an alarming unit generating a predetermined sound or the like) on detecting malfunction of the sensor 12 may be provided in the transmitter 14 itself.

The sensor inserting device 10 according to the embodiment is configured as described above. Now, the process of inserting the indwelling sensor 12 using the sensor inserting device 10 will be described.

Figure 10:
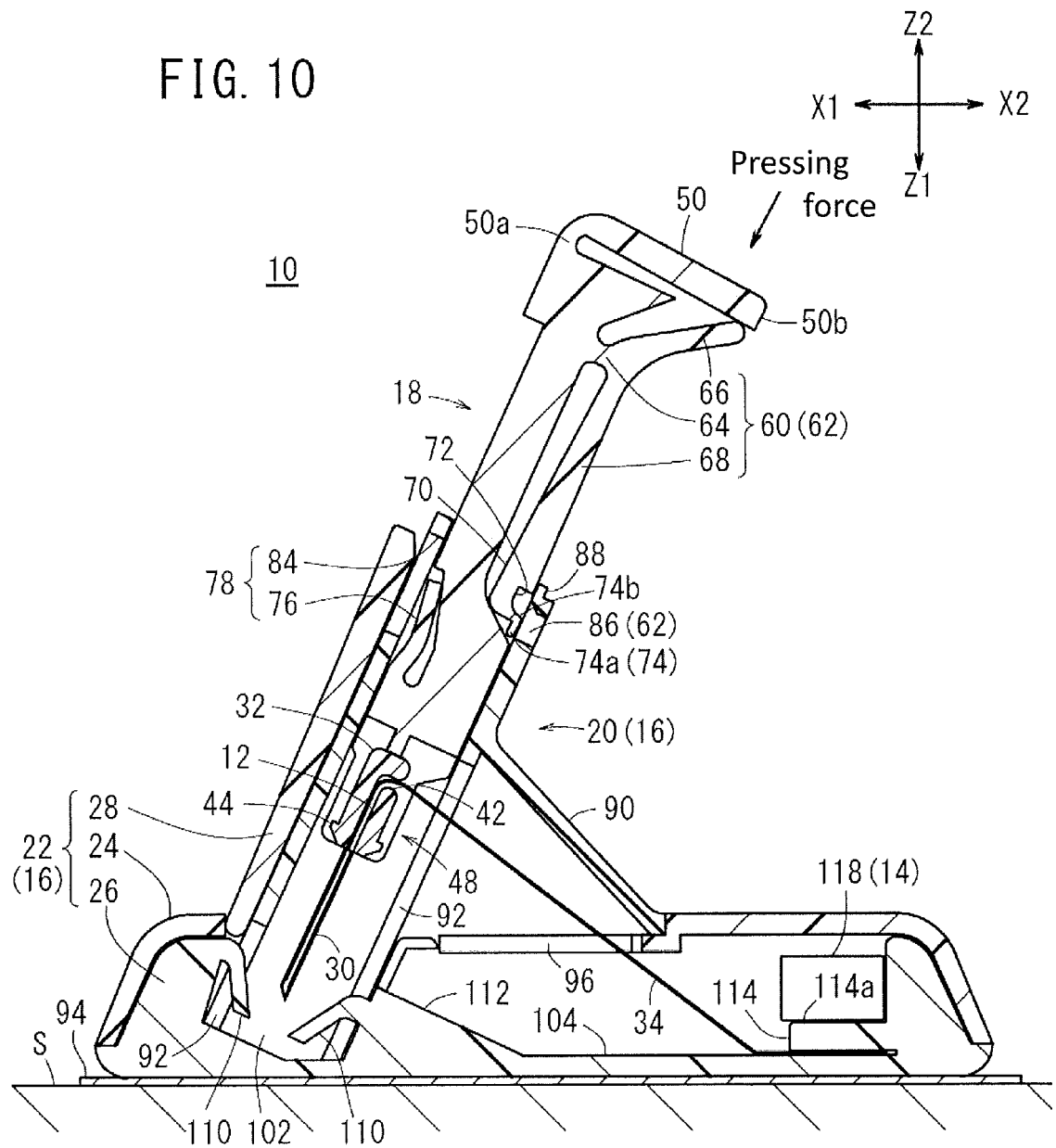
FIG. 10 is a cross sectional view illustrating a state in which a controller of the sensor inserting device illustrated in FIG. 3 is pushed.
Figure 11:
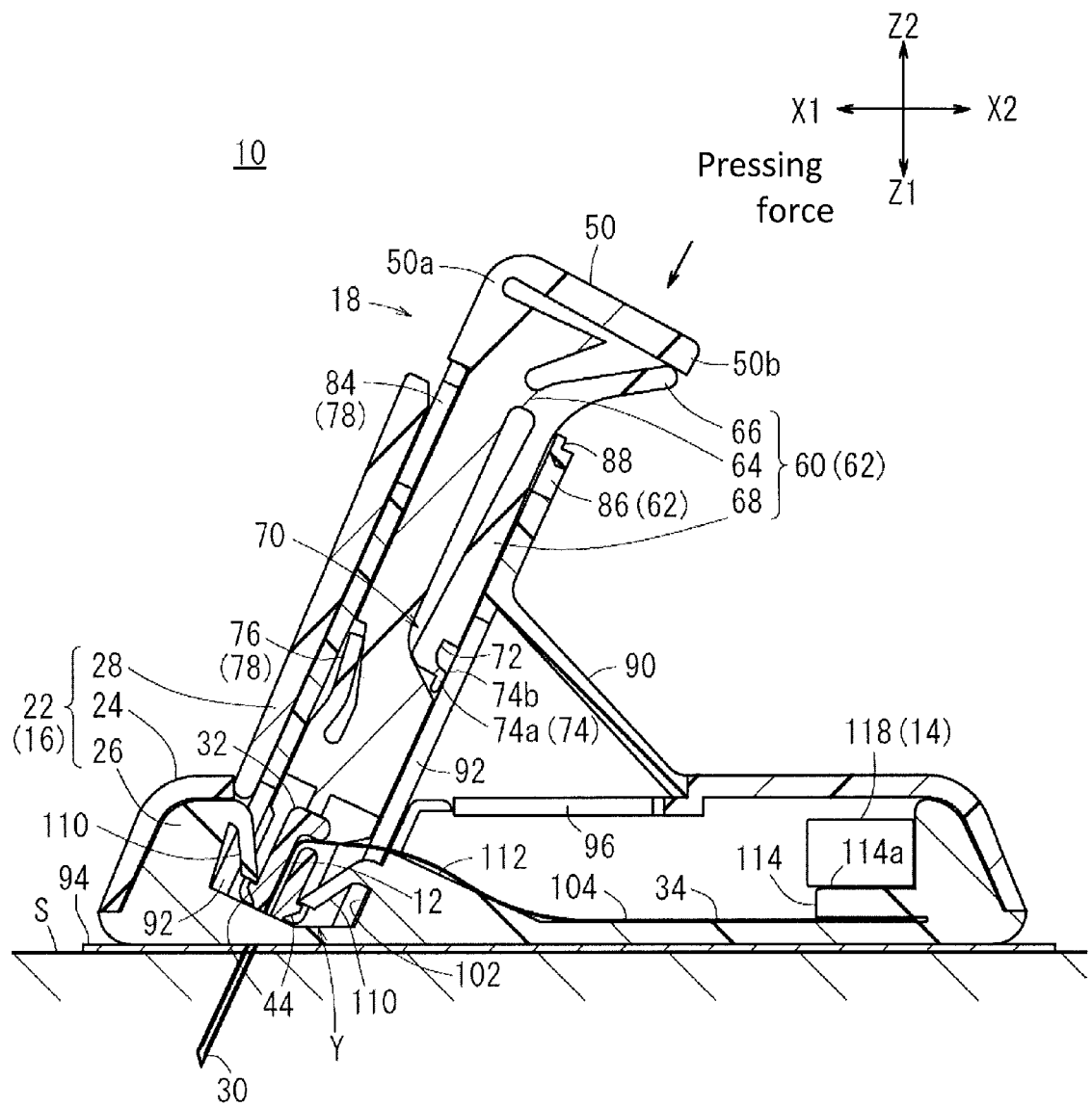
FIG. 11 is a cross sectional view illustrating a state in which the push handle advanced in the sensor inserting device illustrated in FIG. 10.
Figure 12:
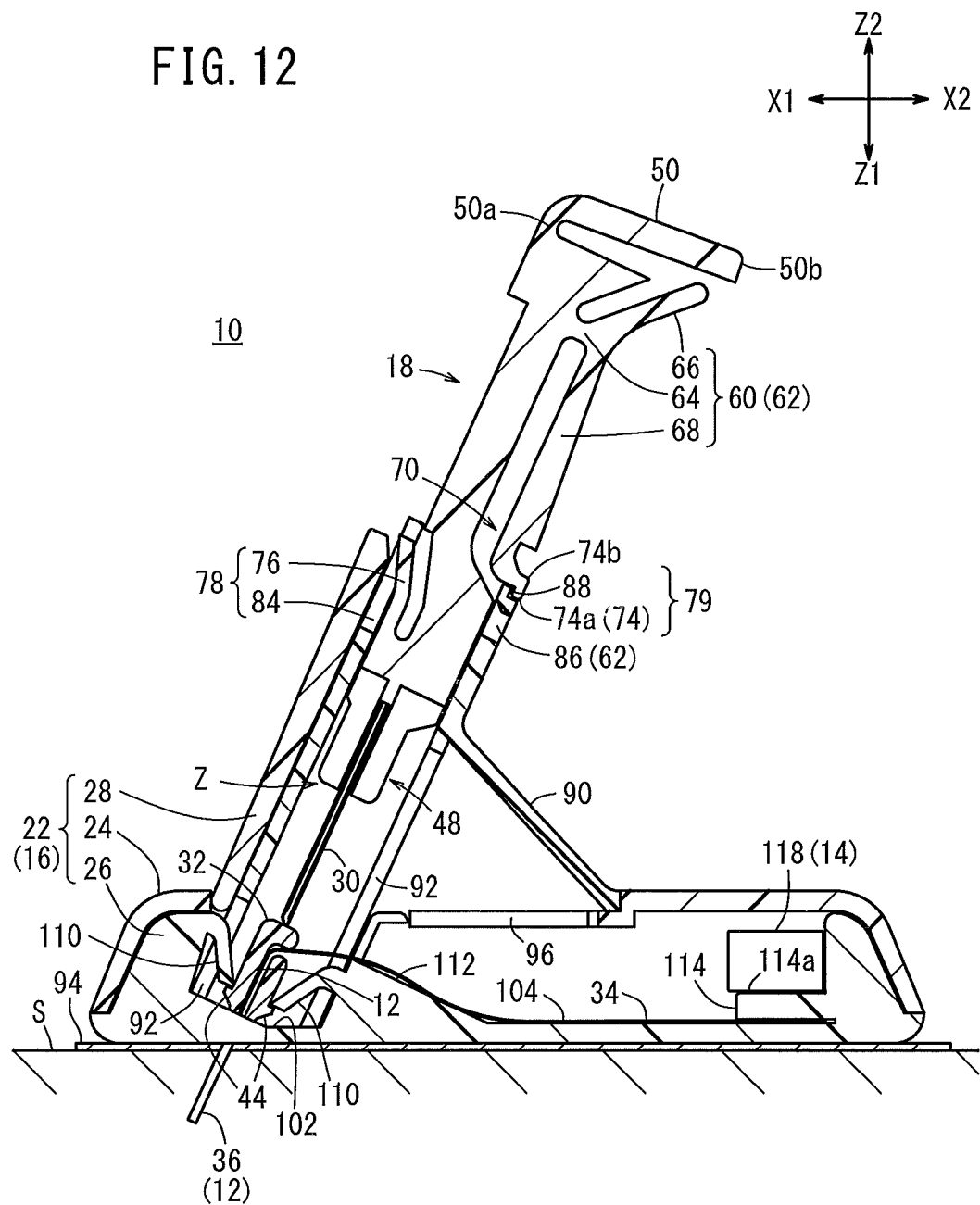
FIG. 12 is a cross sectional view illustrating a state in which the push handle retreats into the sensor inserting device illustrated in FIG. 11.
Figure 13:
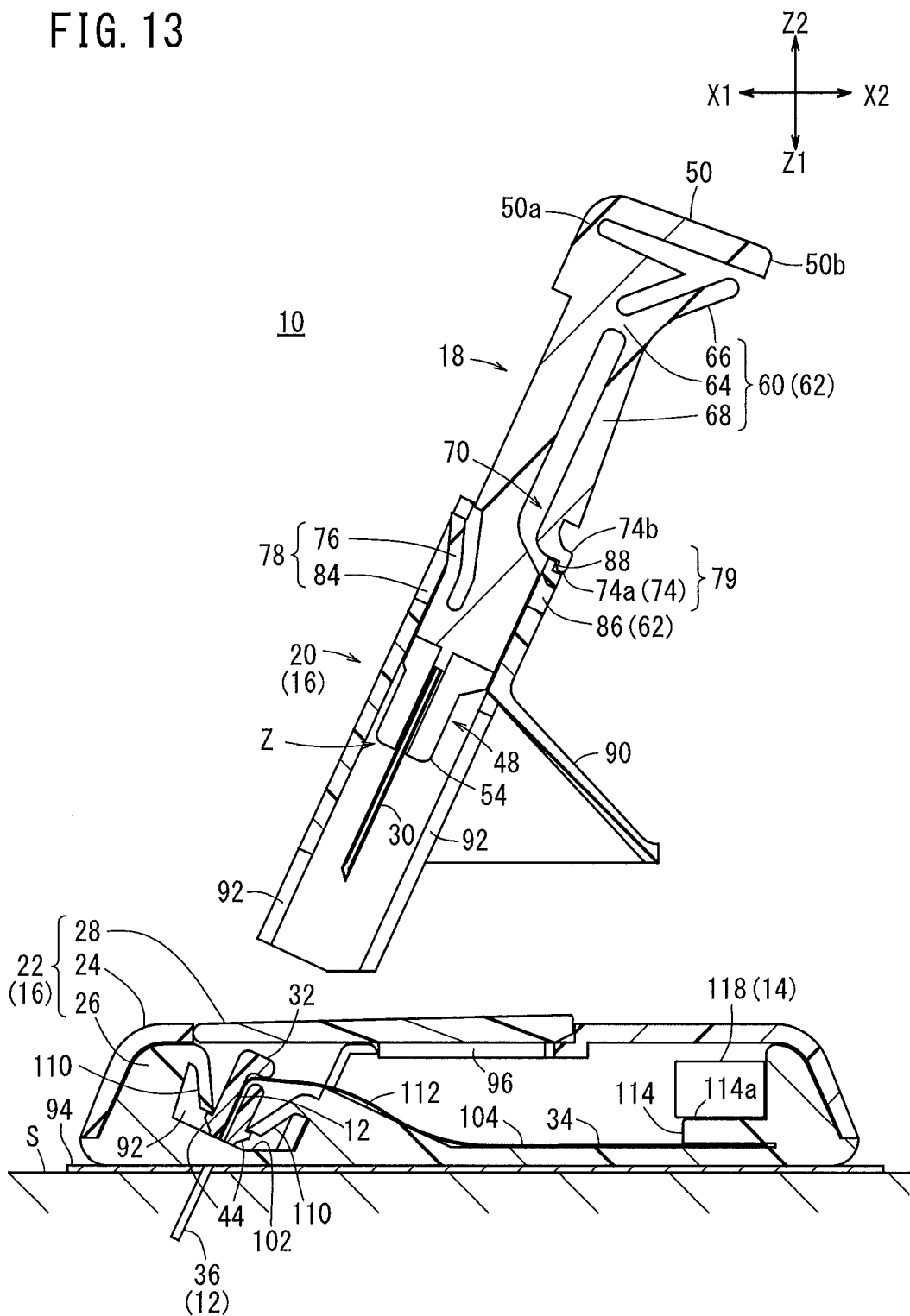
FIG. 13 is a cross sectional view illustrating a state, in which a guide sleeve and the push handle of the sensor inserting device illustrated in FIG. 12, are separated from the indwelling member.
Figure 14:
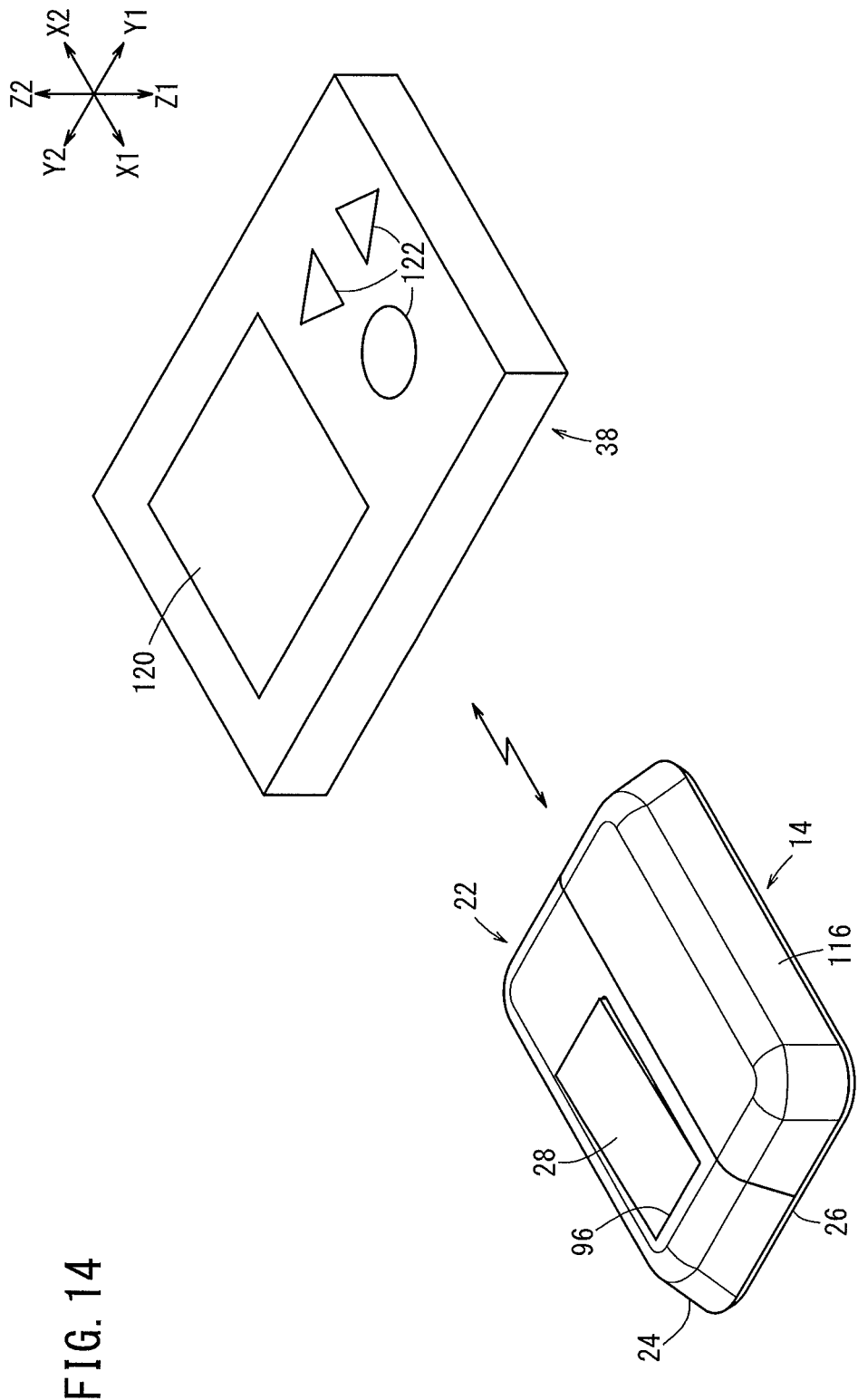
FIG. 14 is an explanatory drawing illustrating the indwelling member placed (set) on a patient and the display unit.

FIG. 10 is a cross sectional view illustrating the state in which the controller 50 of the sensor inserting device 10, illustrated in FIG. 3, is pushed. FIG. 11 is a cross sectional view illustrating a state in which the push handle 18 advanced in the sensor inserting device 10 illustrated in FIG. 10. FIG. 12 is a cross sectional view illustrating a state in which the push handle 18 retreated in the sensor inserting device 10 illustrated in FIG. 11. FIG. 13 is a cross sectional view illustrating a state in which the guide sleeve 20 and the push handle 18 of the sensor inserting device 10 illustrated in FIG. 12 are separated from the indwelling member 22. FIG. 14 is an explanatory drawing illustrating the indwelling member 22 placed (set) on the patient and the display unit 38.

When the sensor inserting device 10 according to the embodiment is used, as illustrated in FIG. 8, the transmitter 14 is set (attached) to the sensor inserting device 10 in which the sensor 12 (sensor cover 32) and the insertion needle 30 are held in the push handle 18 (in a held state). The transmitter 14 is disposed on the top face of the base plate 100 of the indwelling member 22. In this step, the terminal 118 is inserted in the aperture 104*a* of the container passage 104 of the indwelling member 22 to electrically connect the transmitter 14 and the fix-connection unit 114.

As illustrated in FIG. 9, after the transmitter 14 is connected, an initial check is performed by using the display unit 38 to determine the operating state of the sensor 12. In this initial check, by the transmitter 14 supplying power to the sensor 12, the transmitter 14 receives a signal from the sensor 12 and transmits the signal to the display unit 38. When the display unit 38 receives the signal from the transmitter 14, the display unit 38 determines the operating state of the sensor 12 based on the signal. If the sensor 12 is in a normal state, the message telling that the sensor 12 can be inserted into the patient is displayed. If the sensor 12 is in an abnormal state, the message telling that a malfunction (error) has occurred in the sensor 12 is displayed.

When the sensor 12 is in a normal state, insertion and indwelling of the sensor 12 is carried out using the sensor inserting device 10. In this case, the sensor inserting device 10 with an adhesive sheet 94 sticking on to the bottom face of the indwelling member 22 is positioned at a predetermined location (location of insertion) on the abdomen of a patient and the indwelling member 22 sticks on to the skin S of the abdomen.

In this state, as illustrated in FIG. 10, the user pushes the controller 50 (pusher end 50*b*) of the push handle 18 to rotate the upper extending piece 66 and the lower extending piece 68 of the rotary-engagement-portion 60. In this manner, the hooking portion 70 of the lower extending piece 68 comes out of the retaining hole 86, allowing the push handle 18 to advance.

When the user further pushes the controller 50, the whole body of the push handle 18 advances toward the distal end. That is, the sensor inserting device 10 is configured that, by the operation of the user pushing the pusher end 50*b*, releasing of the push handle 18 from the held state, and advancing the push handle 18 can be performed.

As illustrated in FIG. 11, when the guide sleeve 20 moves toward the distal end along with the advance motion of the push handle 18, the holding portion 48 contacts the insertion hole 102 of the indwelling member 22, stopping the advance motion of the push handle 18 at an insert position Y. At the insert position Y, the receiving portion 112 contacts the cable 34 extending from the sensor 12 to suppress abnormal location of the cable 34 caused by the advance motion. With the advance motion of the push handle 18, the detector 36 and the insertion needle 30 pierce (are inserted into) the body of the patient. Further, at the insert position Y, the protrusion 44 of the sensor cover 32 engages with the hook 110 of the indwelling member 22.

As illustrated in FIG. 12, after the advance motion of the push handle 18, the push handle 18 retreats toward the proximal end operated by the user. In this step, the protrusion 44 of the sensor cover 32 engages with the hook 110 to retain the sensor 12 and the sensor cover 32 in the indwelling member 22, so that only the insertion needle 30 moves toward the proximal end together with the push handle 18. When the push handle 18 retreats, the curved face 74*b* of the hooking portion 70, moving through the guide hole 82, easily go over the retaining hole 86 and, as illustrated in FIG. 12, the lower extending piece 68 is exposed on the upper end portion of the guide sleeve 20. When the push handle 18 retreats, the anti-separation piece 76 enters into the restriction hole 84 at the distanced position Z in which the insertion needle 30 is separated from the skin S, so as to contact the lip of the upper end portion of the restriction hole 84, thereby restricting further retreat motion of the push handle 18. In this manner, the push handle 18 is prevented from coming out of the guide sleeve 20. Further, since the hooking portion 70 is exposed on the upper end portion of the guide sleeve 20, the projecting portion 74*a* of the lower extending piece 68 engages with the notch 88 of the guide sleeve 20, thereby restricting advance motion of the push handle 18.

Then, as illustrated in FIG. 13, the sensor inserting device 10 is configured that the push handle 18 and the guide sleeve 20 are removed from the indwelling member 22. The sensor inserting device 10 is configured that the engagement of the distal end projecting portion 80 (see FIG. 2) and the internal projecting portion 108 (see FIG. 7A) can be released relatively with ease by pulling the guide sleeve 20 in the axial direction off of the indwelling member 22. The insertion window 96 is covered by the lid 28 after the guide sleeve 20 has been removed, and in this state, the indwelling member 22 and the transmitter 14 are placed on the skin S of the patient.

As illustrated in FIG. 14, the transmitter 14, placed on the skin S of the patient, transmits a signal of blood sugar level detected by the sensor 12 to the display unit 38. The display unit 38 can check whether the sensor 12 is inserted into the body of the patient by comparing the signal value before the insertion of the sensor 12 and the signal value after the insertion of the sensor 12. The signal after the insertion of the sensor 12 into the body of the patient is significantly greater than the signal before the insertion of the sensor 12. So that, by examining the amount of change in the signal and comparing with the threshold value set for normal insertion, whether the sensor 12 (detector 36) is correctly inserted into the patient can be checked.

In a conventional method of inserting the sensor 12, it takes about three hours before the sensor 12 indwelling in the body of the person to be measured starts measuring stably. Without a stable signal, determining whether the sensor 12 is inserted correctly into the person to be measured is not possible. Thus, a patient must wait during the waiting time of about three hours to determining if the sensor is functioning correctly—this delay is a problem.

However, by using the sensor inserting device 10, the information on whether the sensor 12 is inserted correctly can immediately be provided to the user by detecting the signal from the sensor 12 before and after the insertion of the sensor 12. If the insertion of the sensor 12 has failed, the user can immediately perform insertion of the sensor 12 again. This provides efficient insertion of the sensor 12. Of course, the user wants to determine the operating state of the sensor again after the sensor 12 is inserted, which allows for the checking of broken wires or the like that may be caused by the inserting operation of the sensor 12.

Figure 15:
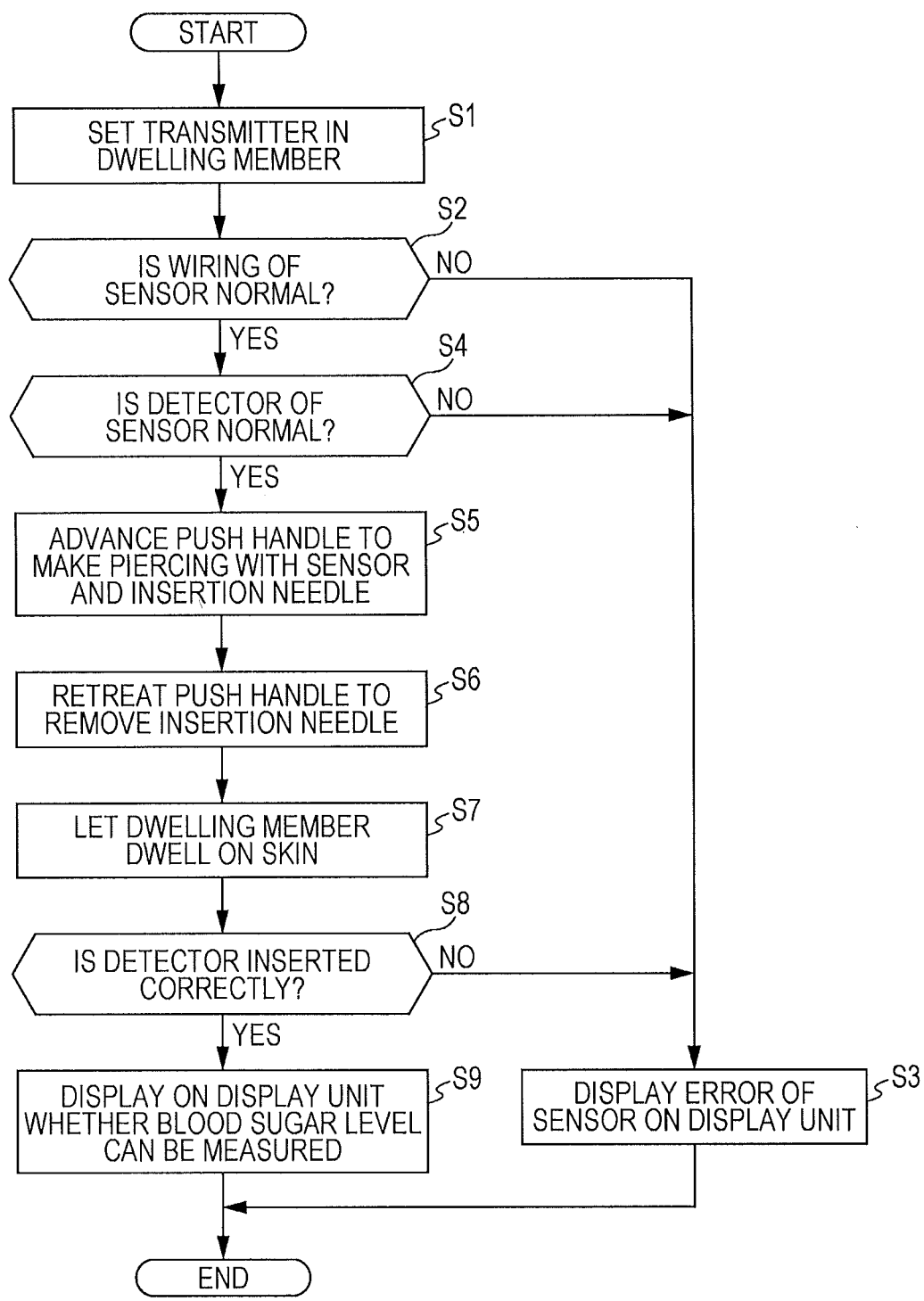
FIG. 15 is a flowchart illustrating the operating method of the sensor inserting device.

FIG. 15 is a flowchart illustrating the operating method of the sensor inserting device 10. The flow of the inserting process of the sensor inserting device 10 will be comprehensively described below based on FIG. 15. The sensor inserting device 10 is configured such that the sensor 12 and the transmitter 14 are electrically connected (connected to transmit a signal) by setting (attaching) the transmitter 14 in the indwelling member 22 (device main body 16) (step S1: connecting step).

Then, the display unit 38 receives a signal transmitted from the transmitter 14 connected to the sensor 12 to determine the operating state of the wiring (including the sensor circuit) from the sensor 12 to the cable 34 (step S2: checking step). In step S2, if the sensor 12 or other portion(s) is in an abnormal state, the process proceeds NO to step S3, and if the sensor 12 or other portion(s) is in a normal state, the process proceeds YES to step S4.

In the step S3, the display unit 38 displays an error associated with the sensor 12 on the display panel 120 to prompt the user to address the error. In the step S4, the display unit 38 further determines if there is insufficient sensitivity (e.g., degradation) in the detector 36 of the sensor 12 (step S4: second checking step). In step S4, if the detector 36 has insufficient sensitivity (i.e., is in abnormal state), the process proceeds NO to step S3, and, if sensitivity is normal, the process proceeds YES to step S5.

Then, the user advances the push handle 18 to insert the sensor 12 (detector 36) and the insertion needle 30 into the body of the patient (step S5: advance motion step). After that, the user retreats the push handle 18 to remove the insertion needle 30 from the sensor 12 (step S6: retreat motion step).

Further, the push handle 18 and the guide sleeve 20 are removed from the indwelling member 22, and the indwelling member 22 and the transmitter 14 remain on the skin S of the patient (step S7: dwelling step). After step S7, based on the signal transmitted from the transmitter 14 connected to the sensor 12, the display unit 38 and/or transmitter 14 determine whether the detector 36 is correctly inserted into the patient (step S8: insertion determination step). In step S8, if it is determined that the insertion of the sensor 12 failed, the process proceeds NO to the step S3, and, if it is determined that the sensor 12 is inserted successfully, the process proceeds YES to step S9.

In step S9, a message, explaining that the measurement of blood sugar level can be performed correctly, is displayed on the display panel 120 of the display unit 38. Thus, the insertion and indwelling of the sensor 12 performed by the sensor inserting device 10 is complete.

As described above, the sensor inserting device 10 according to the embodiment is configured that, when the transmitter 14 is set in the indwelling member 22, the sensor 12, in the held state before insertion, and the transmitter 14 are connected so as to allow transmission of a signal by the cable 34. In this manner, the operating state of the sensor 12 can be checked by the display unit 38 via the transmitter 14 before the detector 36 of the sensor 12 and the insertion needle 30 are inserted into the body of the patient. As a result, if there is a problem (abnormality) in the sensor 12, insertion of the sensor 12 can be prevented, so that stress and pain of the patient can be reduced. Further, the sensor 12 having a problem can immediately be replaced with a normal sensor 12, so that working efficiency of insertion and indwelling of the sensor 12 can be improved.

In embodiments, the fix-connection unit 114, included in the indwelling member 22, electrically connects the transmitter 14 and the cable 34 when the transmitter 14 is set. In this manner, the sensor 12 and the transmitter 14 can easily be connected.

The sensor inserting device 10 according to the embodiment is configured such that the distance from the sensor 12 to the fix-connection unit 114, when the sensor 12 is in the held state, and the distance from the inserted sensor 12 to the fix-connection unit 114, when insertion is made, are approximately the same. In this manner, the length of the cable 34 can suitably be determined, minimizing a slack of the cable 34 between the sensor 12 and the fix-connection unit 114, thereby allowing the cable 34 to easily be contained in the container passage 104 of the indwelling member 22.

Further, by providing the retreat preventing mechanism 78 and the advance preventing mechanism 79 that prevent the push handle 18 from retreating and advancing, respectively, at the distanced position where the push handle 18 is positioned after the retreat motion, the push handle 18 is prevented from coming off the device main body 16, and the problem of inadvertently piercing with the insertion needle 30 again by unintentionally advancing the push handle 18 can be avoided.

Furthermore, the retaining mechanism 62 also works to avoid the problem of unintentionally advancing the push handle 18 held in the guide sleeve 20. In other words, the retaining mechanism 62 functions as a safety mechanism of the sensor inserting device 10 to allow or avoid piercing with the insertion needle 30.

Figure 16:
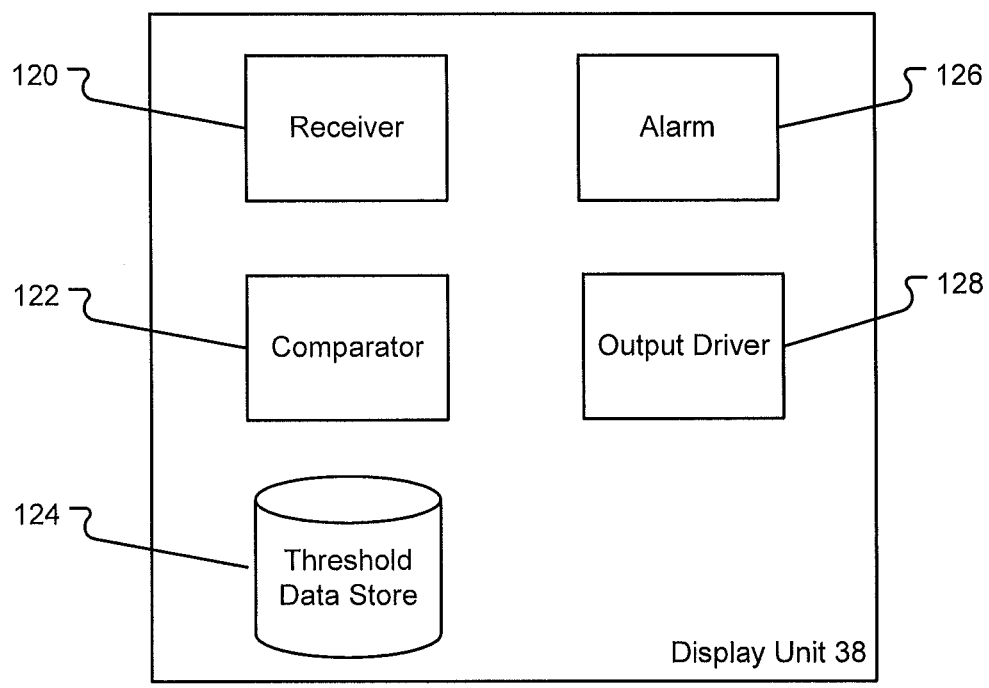
FIG. 16 is a block diagram of embodiments of the software modules for a display unit.

An embodiment of one or more modules 120-128 of a display unit 38 are shown in FIG. 16. The one or more modules 120-128 can be one or more components, which may be hardware, software, or a combination of hardware and software. The one or more modules 120-128 can be executed by a processor, such as that described in conjunction with FIG. 19. Alternatively or additionally, the components described in conjunction with FIG. 16 can be logic circuits or other specially-designed hardware that are embodied in a FPGA, ASIC, or other hardware. The one or more modules 120-128 may include a receiver module 120, a comparator 122, an alarm 126, an output driver 128, and/or a threshold data store 124.

The receiver module 120 may be operable to receive the signal from the transmitter 14. The signal, as described above, is produced by the sensor 12 before insertion of the sensor 12, after insertion of the sensor 12 but before the sensor 12 sends a stable reading, and after a stable reading is provided by the sensor 12. In some situations, the signal is an analog signal that may be perpetually or constantly updating. In other circumstances, the signal may be a digital signal provided periodically, for example, every second. The signal may be received in any configuration or format. The receiver 120 can receive the signal wirelessly or by a wired connection. Thus, the receiver 120 can include any hardware, drivers, and/or software that allows for the reception of the signal from the transmitter 14. The receiver 120 can provide the signal to the comparator 122.

Figure 17:
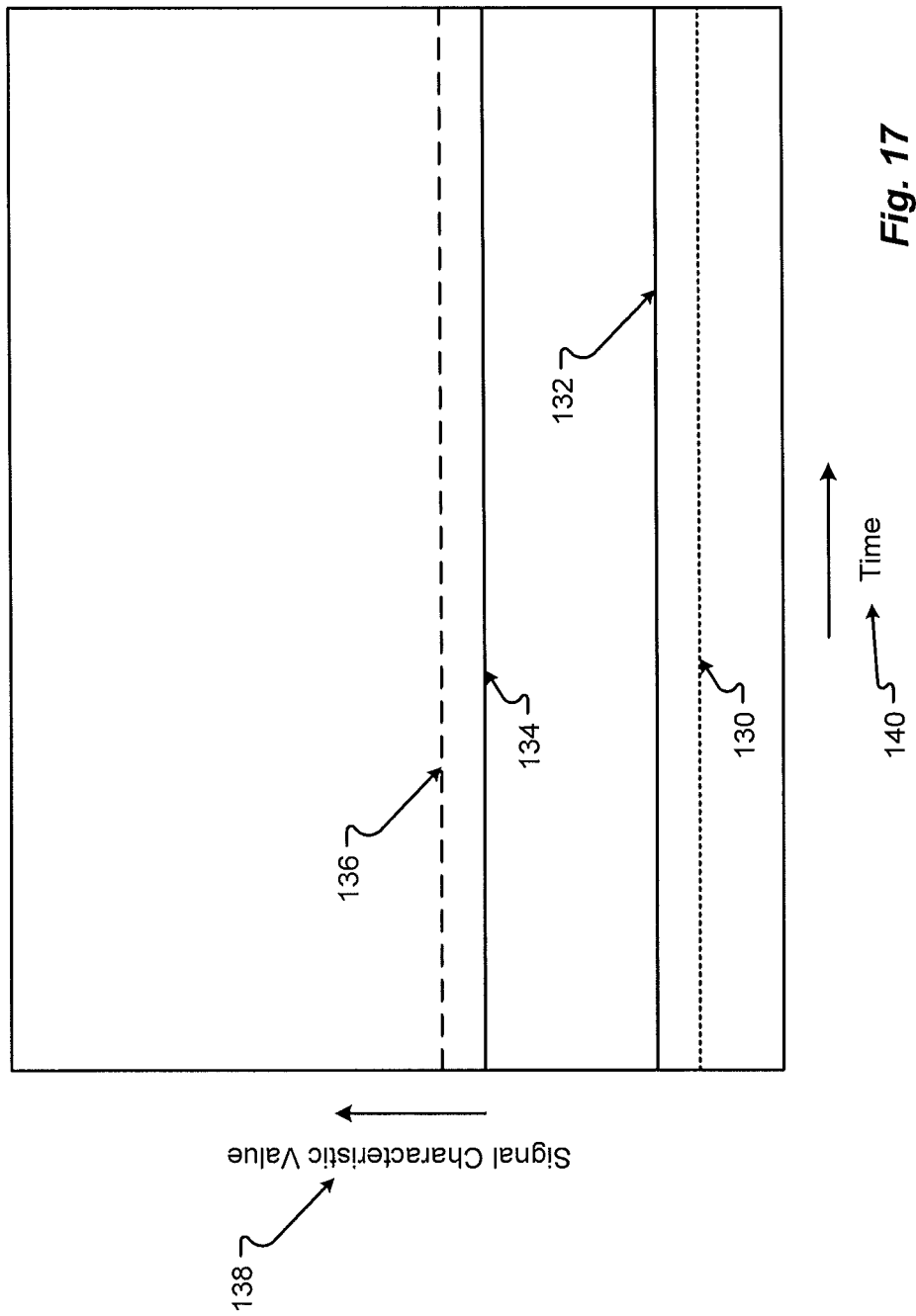
FIG. 17 is a graphical representation of an embodiment of a process for checking signal characteristics against thresholds.

A comparator 122 can access threshold data 124 to determine if the signal is within prescribed or predetermined norms. For example, as shown in FIG. 17, the comparator 122 can receive a first signal 132 before a sensor 12 is inserted into the patient. The first signal 132 may be compared to a first threshold 130. The first signal 132 may be a single reading or a several readings received over a period of time. The comparator 122 can determine based on the value(s) of the first signal 132 if the first signal 132 is above the threshold 130 (or within determined norms).

The threshold 130 can represent some value, whether predetermined or derived from previous signal readings, that would indicate the sensor 12 is functioning correctly. In one situation, the threshold 130 may be a zero voltage or amperage, indicating that any value above zero means that the sensor 12 is functioning. The threshold 130 may be derived if the display unit 38 stores previous measures in the threshold data 124. The previous measures can provide a different threshold based on actual measured values. To determine the threshold 130, the comparator 122 may employ an algorithm applied to the previous measures. For example, the comparator 122 may determine the threshold 130 should be 50% of the average of the past 20 measurements for the sensor 12 before the sensor 12 was inserted.

The comparator 122 can also compare a second signal 134, shown in FIG. 17, to another threshold 136. The second signal 134 may represent the signal received from the sensor 12 after the sensor 12 is inserted into the patient but before the sensor 12 begins providing a stable reading. The second signal 134 may also be compared to a threshold 136 that may be derived or predetermined, as explained with the first threshold 130. The second signal 134 may represent a functioning sensor 12, if the second signal 134 is above the threshold 136. In the example shown in FIG. 17, the second signal 134 is below the threshold 136 and may represent a non-functioning state.

The example chart, in FIG. 17, can represent the comparisons of the signals 132, 134 to the thresholds 130, 136. The signals 132, 134 may represent any type of signal characteristic, for example, voltage, amperage, etc., (that can be plotted, calculated or received) on the axis represented by arrow 138. The other axis 140 may represent a time period. As such, the signals 132, 134 may be tracked over a period of time and the determinations of normal signals may be made on average values or at some particular instance during the period of time. The first signal 132 and second signal 134 are representations of possible signals. In some circumstances, the second signal 134 may have a greater value than the first signal 132. For example, if sensor 12 is a fluorescence sensor, the first signal 132 before insertion has a greater value than the second signal 134 received after the insertion of the sensor 12. This difference is due to the sensor 12 receiving scattered light before insertion and, after insertion, the sensor 12 is stabilized and shielded from the scattered light by body fluids. Further, the difference or amount of change between the first signal 132 and the second signal 134 may be measured to determine if the sensor 12 is functioning. If the amount of change is correct (i.e., is above or below a threshold), whether an increase or decrease in the characteristic, the comparator 122 can determine that the sensor is functioning normally.

In still another situation, a measurement of the first signal 132 may be made before insertion. Then, a measurement of the second signal 134 is made at a predetermined time after insertion of the sensor 12. The rate of change between the measurement of the first signal 132 and the measurement of the second signal 134 is plotted or determined. The rate of change may then be compared to a threshold to determine if the rate of change is within predetermined norms or acceptable limits. For example, the measurement of a voltage may be made before insertion of the sensor 12. Then, thirty seconds after insertion of the sensor 12, the measurement of the voltage may be made again. The change in the voltage characteristic is determined for the thirty second period. If the change in the voltage over the thirty second period is under a predetermined threshold, the sensor 12 may be functioning improperly. The display unit 38 can also include a threshold data store 124 that can include one or more items of data. The data can be stored by any method or in any format, such as, a flat file database, an object-oriented database, or by some other formulation, protocol, and/or standard. The data can include previously measured signals or the values for predetermined or derived thresholds. The comparator 122 can access and read the data for comparing signals to thresholds. In other circumstances, the comparator 122 or receiver 120 can store signal characteristics or other information in the threshold data store 124.

The comparator 122 can communicate the results of any comparison to the alarm module 126. The alarm module 126 may determine whether an alarm message or signal should be provided to the user. If the comparator 122 determines that a received signal is not normal, for example, the second signal 134 is below the threshold 136, the comparator 122 may indicate the abnormal signal to the alarm module 126. The alarm module 126 may provide a message or other indication to the user regarding the abnormal signal. The message or indication may be provided to the output driver 128 by the alarm module 126.

The output driver 128 can send or provide the alarm message or indication to a user. For example, the output driver 128 can render a message on a screen of the display unit 38 that information about how the sensor 12 is not functioning properly and to reinsert a new sensor 12. In other circumstances, the output driver 128 can energize a light emitting diode (LED), buzzer, vibration device, etc. to indicate the abnormal function or state. The output driver 128 includes any drivers, software, and/or hardware to send the appropriate signals to the output devices, screens, etc.

Figure 18:
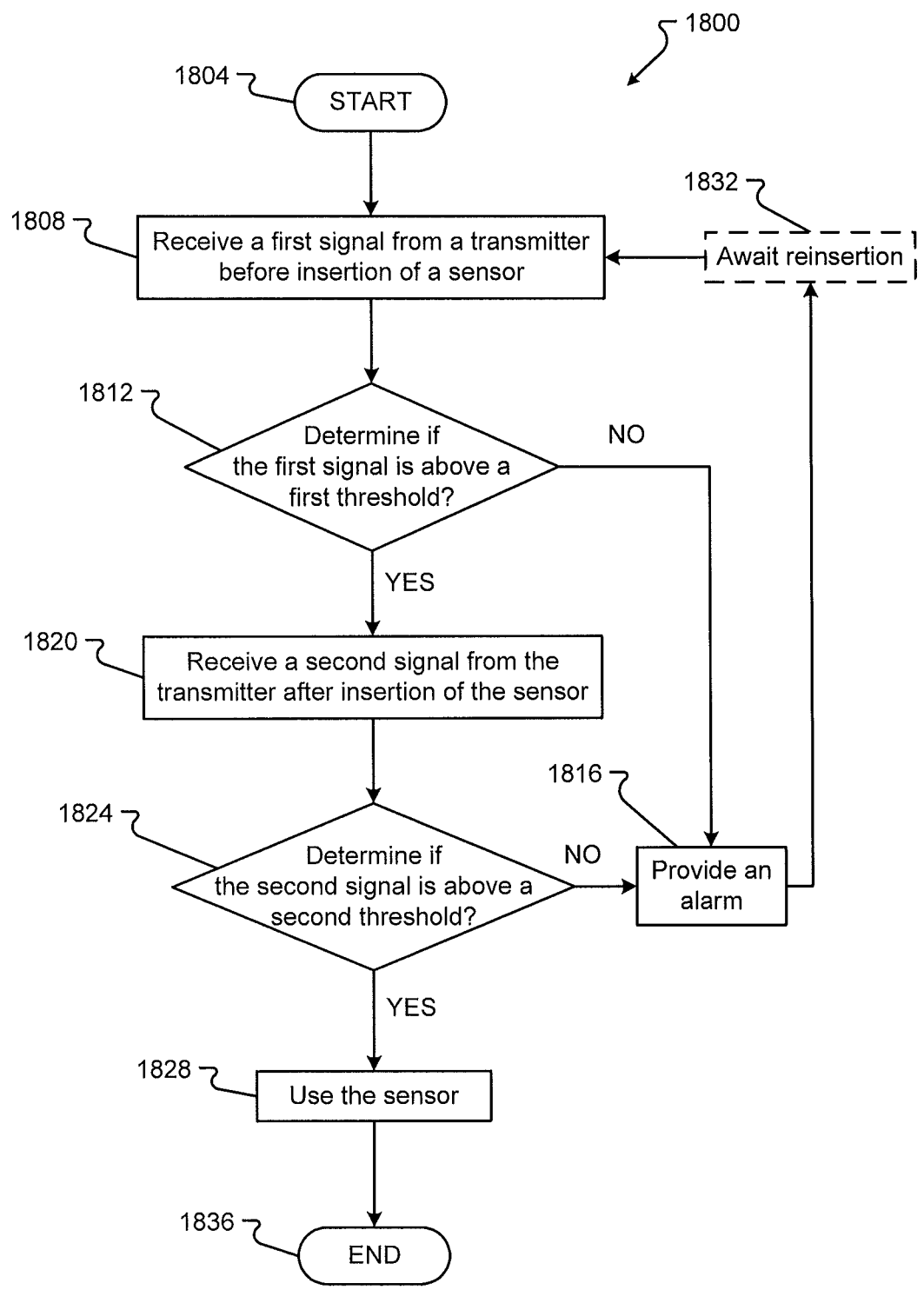
FIG. 18 is a flowchart illustrating an embodiment of a process for checking signal characteristics against thresholds.

An embodiment of the method 1800 for testing a sensor 12 is shown in FIG. 18. A general order for the steps of the method 1800 is shown in FIG. 18. Generally, the method 1800 starts with a start operation 1804 and ends with an end operation 1836. The method 1800 can include more or fewer steps, and/or the steps can be arranged differently than those shown in FIG. 18. The method 1800 can be executed as a set of computer-executable instructions executed by a computer system or processor and encoded or stored on a computer readable medium. Hereinafter, the method 1800 shall be explained with reference to the systems, components, modules, software, data structures, user interfaces, devices, sensors, etc. described in conjunction with FIGS. 1-17.

The receiver module 120 may receive a first signal from a transmitter 14, in step 1808. The first signal may include signal characteristics associated with the signal coming from the sensor 12. The first signal may be received before the sensor 12 is inserted into the patient. After receiving the first signal, the receiver module 120 can send the signal to the comparator module 122.

The comparator module 122 may determine whether the first signal is above a first threshold (or in some predetermined normal state), in step 1812. In some circumstances, the comparator module 122 may determine if the first signal is below or crosses a threshold. As described in conjunctions with FIG. 17, the comparator module 122 can compare the first signal 132 to a first threshold 130 that may be read or retrieved from a threshold data store 124. If the first signal is above the threshold, the method 1800 proceeds YES to step 1820. If the first signal is below the threshold, the method 1800 proceeds NO to step 1816.

In step 1820, the display unit 38 can receive an indication that the sensor 12 has been inserted. After receiving an indication that the sensor 12 has been inserted, the receiver 120 can receive a second signal. The receiver 120 may send the second signal to the comparator 122, which can compare the second signal to a second threshold, in step 1820. The second comparison of the second signal to the second threshold may be as explained above and/or as explained in conjunction with FIG. 17. If the second signal is above the second threshold, the method 1800 proceeds YES to step 1828, where the user may use the sensor to make a measurement. If the second signal is below the threshold, the method 1800 proceeds NO to step 1816.

In step 1816, the comparator 122 can provide the abnormal signal indication to the alarm module 126. The alarm module 126 can create a message or indication for the user that is associated with the abnormal signal. The message or indication can be sent to an output driver 128 to present a user interface on the display unit 38 stating that the sensor 12 is not functioning normally or may present another type of indication, for example, a blinking LED or a vibration. After providing the message or indication, the display unit 38 may optionally await reinsertion of a new sensor 12, in step 1832. If a new sensor 12 is inserted, the display unit 38 may retest the new sensor 12 as described above.

Figure 19:
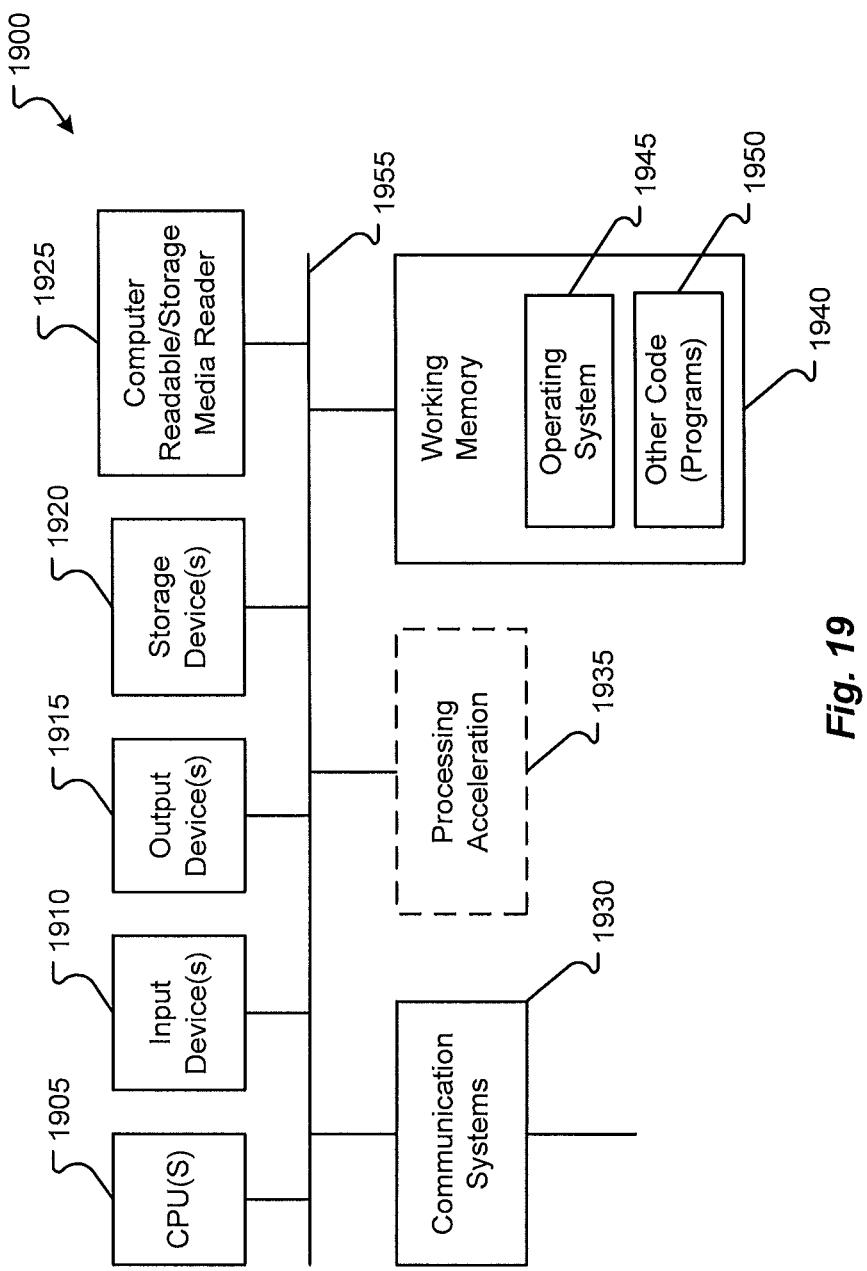
FIG. 19 is a block diagram of an embodiment of the hardware and software modules for a display unit or other computing device.

FIG. 19 illustrates an embodiment of the electronic hardware of a display unit 38 upon which the software and/or methods described herein may be executed. The display unit 38 is shown comprising hardware elements that may be electrically coupled via a bus 1955. The hardware elements may include one or more central processing units (CPUs) 1905; one or more input devices 1910 (e.g., a touch screen, a hardware button, a keyboard, etc.); and one or more output devices 1915 (e.g., a display device, a LED, etc.). Examples of the CPUs and/or processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, library, and/or architecture.

The display unit 38 may also include one or more storage devices 1920. By way of example, storage device(s) 1920 may be disk drives, optical storage devices, solid-state storage devices, such as a random access memory ("RAM") and/or a read-only memory ("ROM"), which can be programmable, flash-updateable, and/or the like.

The display unit 38 may additionally include a computer-readable storage media reader 1925; a communications system 1930 (e.g., a modem, a network card (wireless or wired), an infra-red communication device, etc.); and working memory 1940, which may include RAM and ROM devices as described above. The display unit 38 may also include a processing acceleration unit 1935, which can include a DSP, a special-purpose processor, and/or the like.

The computer-readable storage media reader 1925 can further be connected to a computer-readable storage medium, together (and, optionally, in combination with storage device(s) 1920) comprehensively representing remote, local, fixed, and/or removable storage devices plus storage media for temporarily and/or more permanently containing computer-readable information. The communications system 1930 may permit data to be exchanged with transmitter 14 and/or any other computer that may be connected to or in wireless communication with the display unit 38. Moreover, as disclosed herein, the term "storage medium" may represent one or more devices for storing data, including ROM, RAM, magnetic RAM, core memory, magnetic disk storage mediums, optical storage mediums, flash memory devices and/or other machine readable mediums for storing information.

The display unit 38 may also comprise software elements, shown as being currently located within a working memory 1940, including an operating system 1945 and/or other code 1950, which can include the modules and/or processes described in conjunction with FIGS. 16 and 18. It should be appreciated that alternate embodiments of a display unit 38 may have numerous variations from that described above. For example, customized hardware might also be used and/or particular elements might be implemented in hardware, software (including portable software, such as applets), or both. Further, connection to other computing devices such as network input/output devices may be employed.

Optionally, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In some situations, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

The phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refer to any process or operation done without material human input when the process or operation is performed. However, a process or operation can be automatic, even though performance of the process or operation uses material or immaterial human input, if the input is received before the performance of the process or operation. Human input is deemed to be material if such input influences how the process or operation will be performed. Human input that consents to the performance of the process or operation is not deemed to be "material."

The term "computer-readable medium," as used herein refers to any tangible storage and/or transmission medium that participates in providing instructions to a processor for execution. Such a medium may take many forms, including but not limited to, non-volatile media, volatile media, and transmission media. Non-volatile media includes, for example, non-volatile random access memory (NVRAM), or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a compact disc read only memory (CD-ROM), any other optical medium, punch cards, paper tape, any other physical medium with patterns of holes, a RAM, a programmable read only memory (PROM), and erasable programmable read only memory EPROM, a FLASH-EPROM, a solid state medium like a memory card, any other memory chip or cartridge, a carrier wave as described hereinafter, or any other medium from which a computer can read. A digital file attachment to an e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. It should be noted that any computer readable medium that is not a signal transmission may be considered non-transitory.

The term "module" as used herein refers to any known or later developed hardware, software, firmware, artificial intelligence, fuzzy logic, or combination of hardware and software that is capable of performing the functionality associated with that element.

The terms "determine," "calculate," and "compute," and variations thereof, as used herein, are used interchangeably and include any type of methodology, process, mathematical operation, or technique.

It shall be understood that the term "means," as used herein, shall be given its broadest possible interpretation in accordance with 35 U.S.C., Section 112, Paragraph 6 or other applicable law. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "in communication with," as used herein, refers to any coupling, connection, or interaction using electrical signals to exchange information or data, using any system, hardware, software, protocol, or format, regardless of whether the exchange occurs wirelessly or over a wired connection.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The present invention is not limited to the embodiment described above. It goes without saying that various configurations can be made without departing from the spirit and the scope of the present invention.

The invention claimed is:

1. A sensor inserting device comprising:
a device main body comprises a signal transmitting part;
a movement mechanism provided in the device main body and configured to move a detector of a sensor and an insertion needle, while in a held state, the sensor is held together with the insertion needle for piercing a body of a person to be measured, wherein the sensor is electrically connected to the signal transmitting part; and
a signal processor configured to be attached to and detached from the device main body and electrically connected to the signal transmitting part, wherein a signal, associated with biological information, produced by the sensor is transmitted through the signal transmitting part to the signal processor, and wherein the signal transmitting part transmits a signal between the sensor and the signal processor when the signal processor is attached to the device main body in the held state of the movement mechanism, wherein the signal transmitting part is a flexible cable that electrically connects the sensor to the signal processor when in the held state, moves with the sensor during sensor insertion, and maintains the electrical connection while the sensor is indwelling.

2. The sensor inserting device according to claim 1, further comprising:
an alarming unit operable to determine an operating state of the sensor when the signal processor is attached and operable to inform a user of the fault in the sensor when a circuit, including one or more of a group comprising the signal transmitting part connected to the sensor and the sensor, has a fault.

3. The sensor inserting device according to claim 1, wherein the device main body includes an indwelling member placed on a skin of the person with both the sensor and the signal processor, the indwelling member comprising:
a signal processor attaching unit attaching the signal processor; and
a fix-connection unit fixing one of two ends of the signal transmitting part to electrically connect the signal processor and the signal transmitting part when the signal processor is attached.

4. The sensor inserting device according to claim 3, wherein a first distance from the sensor to the fix-connection unit when the sensor is in the held state and a second distance from the sensor to the fix-connection unit when the detector is inserted in the body of the person to be measured are approximately same.

5. The sensor inserting device according to claim 3, wherein the indwelling member comprises a receiving portion for receiving the signal transmitting part at a location in a vicinity of where the detector is inserted into the person to be measured.

6. The sensor inserting device according to claim 1, wherein the movement mechanism is a push handle that is contained in the device main body and configured to advance toward the person to be measured to insert the detector and the insertion needle and to retreat away from the person to be measured to pull out the insertion needle, and wherein the device main body and the push handle are provided with a retreat preventing mechanism configured to prevent the push handle from retreating at a distanced position in which the insertion needle is separated from the person to be measured.

7. The sensor inserting device according to claim 6, wherein the device main body and the push handle are provided with an advance preventing mechanism to prevent the push handle from inadvertently advancing from the distanced position.

8. The sensor inserting device according to claim 7, wherein the advance preventing mechanism comprises:
a distal end portion of an elastic piece provided on the push handle; and
an engagement portion provided at a proximal end of the device main body, the distal end portion of the elastic piece projecting from a proximal end of the device main body at the distanced position to engage with the engagement portion thereby preventing the push handle from advancing.

9. The sensor inserting device according to claim 1, wherein the movement mechanism is a push handle contained in the device main body and configured to advance toward the person to be measured to insert the detector and the insertion needle and to retreat away from the person to be measured to pull out the insertion needle, wherein the device main body and the push handle are provided with a retaining mechanism configured to retain the push handle at a retaining position in which the push handle in the held state is retained to be separated from a distal end portion of the device main body, and wherein the retaining mechanism allows the push handle to advance by operating a controller provided on the push handle.

10. A method for inserting a sensor with a sensor inserting device that holds the sensor and an insertion needle for measuring biological information at a location distanced from a distal end portion of a device main body by a predetermined distance, the method comprising:
providing the sensor inserting device, the sensor inserting device comprising:
the sensor;
a fix-connection unit;
a signal transmitting part, disposed between the sensor and the fix-connection unit of the device main body, for transmitting a signal including biological information output from the sensor;
connecting a signal processor, for processing the signal, to the device main body, wherein the signal processor is electrically connected to the fix-connection unit to allow transmission of the signal between the sensor and the signal processor, wherein the signal transmitting part is a flexible cable that electrically connects the sensor to the signal processor when in the held state, moves with the sensor during sensor insertion, and maintains the electrical connection while the sensor is indwelling;
advancing the sensor and the insertion needle toward a distal end by a movement mechanism provided in the device main body to project the detector of the sensor and a portion of the insertion needle to a distal end of the device main body and into the person; and
removing the insertion needle from the sensor by retreating the insertion needle toward a proximal end by the movement mechanism while leaving the detector in the person.

11. The method according to claim 10, further comprising:
detecting an operating state of the sensor, between the connecting step and the advancing step; and
informing the user of an abnormality of the sensor, by an alarming unit, if there is an abnormality in a circuit, including one or more of a group comprising the signal transmitting part connected to the sensor and the sensor.

12. The method according to claim 10, further comprising:
detecting an operating state of the sensor, after the removing step; and
informing the user of an abnormality of the sensor, by an alarming unit, if there is an abnormality in a circuit, including one or more of a group comprising the signal transmitting part connected to the sensor and the sensor.

13. The method according to claim 12, wherein the detecting is conducted before a stable signal is received from the sensor.

14. An analyte sensing system comprising:
a sensor inserting device comprising:
a device main body comprising a signal transmitting part;
a movement mechanism provided in the device main body and configured to move a detector of a sensor and an insertion needle, while in a held state, the sensor is held together with the insertion needle for piercing a body of a person to be measured, wherein the sensor is electrically connected to the signal transmitting part; and
a signal processor configured to be attached to and detached from the device main body and electrically connected to the signal transmitting part, wherein a signal, associated with biological information, produced by the sensor is transmitted through the signal transmitting part to the signal processor, and wherein the signal transmitting part that transmits a signal between the sensor and the signal processor when the signal processor is attached to the device main body in the held state of the movement mechanism, wherein the signal transmitting part is a flexible cable that electrically connects the sensor to the signal processor when in the held state, moves with the sensor during sensor insertion, and maintains the electrical connection continuously while the sensor is in the held state, while the sensor is inserted, while an insertion needles is withdrawn, and while the sensor indwelling; and an alarming unit in communication with the sensor inserting device, the alarming unit operable to determine an operating state of the sensor when the signal processor is attached and operable to inform a user of the fault in the sensor when a circuit, including one or more of a group comprising the signal transmitting part connected to the sensor and the sensor, has a fault.

15. The analyte sensing system according to claim 14, wherein the alarming unit is operable to determine a first operating state of the sensor before the sensor is inserted into the person.

16. The analyte sensing system according to claim 15, wherein the alarming unit is operable to compare a first signal from the sensor to a first threshold during the first operating state.

17. The analyte sensing system according to claim 16, wherein, if the first signal is below the first threshold during the first operating state, the alarming unit is operable to provide an alert to the user that the fault in the sensor has occurred.

18. The analyte sensing system according to claim 14, wherein the alarming unit is operable to determine a second operating state of the sensor after the sensor is inserted into the person but before the sensor provides a stable signal.

19. The analyte sensing system according to claim 18, wherein the alarming unit is operable to compare a second signal from the sensor to a second threshold during the second operating state.

20. The analyte sensing system according to claim 19, wherein, if the second signal is below the second threshold during the second operating state, the alarming unit is operable to provide an alert to the user that the fault in the sensor has occurred.

* * * * *